United States Patent
Igarashi et al.

(10) Patent No.: US 10,308,670 B2
(45) Date of Patent: Jun. 4, 2019

(54) SILANOL COMPOUND, COMPOSITION, AND METHOD FOR PRODUCING SILANOL COMPOUND

(71) Applicant: NATIONAL INSTITUTE OF ADVANCED INDUSTRIAL SCIENCE AND TECHNOLOGY, Tokyo (JP)

(72) Inventors: Masayasu Igarashi, Ibaraki (JP); Shigeru Shimada, Ibaraki (JP); Kazuhiko Sato, Ibaraki (JP); Tomohiro Matsumoto, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/116,063

(22) PCT Filed: Feb. 3, 2015

(86) PCT No.: PCT/JP2015/052996
§ 371 (c)(1),
(2) Date: Aug. 2, 2016

(87) PCT Pub. No.: WO2015/115664
PCT Pub. Date: Aug. 6, 2015

(65) Prior Publication Data
US 2017/0183363 A1 Jun. 29, 2017

(30) Foreign Application Priority Data
Feb. 3, 2014 (JP) .................. 2014-018925

(51) Int. Cl.
C07F 7/08 (2006.01)
B01J 23/44 (2006.01)
(Continued)

(52) U.S. Cl.
CPC ............. *C07F 7/0836* (2013.01); *B01J 23/40* (2013.01); *B01J 23/44* (2013.01); *B01J 23/462* (2013.01);
(Continued)

(58) Field of Classification Search
None
See application file for complete search history.

(56) References Cited

U.S. PATENT DOCUMENTS 3,209,018 A * 9/1965 Merker .................... B01J 31/02
556/432
3,400,145 A * 9/1968 Wu ............................ C07F 7/21
528/20
(Continued)

FOREIGN PATENT DOCUMENTS

CN 103212314 A 7/2013

OTHER PUBLICATIONS

Moravetski et al., "Si NMR Chemical Shifts of Silicate Species: Ab Initio Study of Environment and Structure Effects", J. Am. Chem. Soc., vol. 118, 1996, pp. 13015-13020.
(Continued)

*Primary Examiner* — Joseph D Anthony
(74) *Attorney, Agent, or Firm* — Marshall, Gerstein & Borun LLP

(57) ABSTRACT

The purpose of the present invention is to provide silanol compounds that can be used as raw materials of siloxane compounds and the like, and a composition of the silanol compounds, as well as to provide a production method that makes it possible to produce silanol compounds at excellent yield. A composition comprising 5 mass % to 100 mass % of a silanol compound represented by Formulas (A) to (C) can be prepared by devising to produce silanol compounds
(Continued)

US 10,308,670 B2
Page 2 under water-free conditions, to produce silanol compounds in a solvent having the effect of suppressing the condensation of silanol compounds, and to perform other such processes, the composition being able to be used as a raw material or the like of siloxane compounds because the silanol compounds can be stably present in the resulting composition.

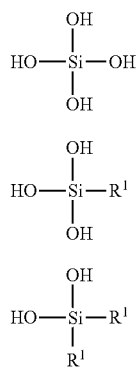

(A)

(B)

(C)

6 Claims, 10 Drawing Sheets

(51) Int. Cl.
| | |
|---|---|
| *B01J 23/46* | (2006.01) |
| *C01B 33/12* | (2006.01) |
| *C07F 7/18* | (2006.01) |
| *B01J 37/03* | (2006.01) |
| *B01J 23/40* | (2006.01) |
| *B01J 23/52* | (2006.01) |
| *B01J 37/02* | (2006.01) |

(52) U.S. Cl.
CPC ............ *B01J 23/464* (2013.01); *B01J 23/52* (2013.01); *B01J 37/0201* (2013.01); *B01J 37/03* (2013.01); *C01B 33/12* (2013.01); *C07F 7/0874* (2013.01); *C07F 7/1892* (2013.01)

(56) References Cited

U.S. PATENT DOCUMENTS

| | | | | |
|---|---|---|---|---|
| 3,853,932 | A | * 12/1974 | Razzano | ............... C07F 7/0874 |
| | | | | 556/459 |
| 3,939,195 | A | 2/1976 | Lucking et al. | |
| 3,983,148 | A | * 9/1976 | Reedy | ....................... C07F 7/21 |
| | | | | 556/451 |
| 4,111,973 | A | * 9/1978 | Bluestein | .................. C07F 7/21 |
| | | | | 556/460 |
| 4,956,231 | A | * 9/1990 | Cavezzan | ............ A61K 9/7069 |
| | | | | 428/343 |
| 4,977,290 | A | * 12/1990 | Evans | ....................... C07F 7/21 |
| | | | | 556/459 |
| 5,852,153 | A | * 12/1998 | Sugo | ......................... C07F 7/21 |
| | | | | 528/14 |
| 2012/0145401 | A1* | 6/2012 | Reyes | .................... C09K 8/528 |
| | | | | 166/305.1 |

OTHER PUBLICATIONS

Office Action in CN Application No. 201580006907.1 dated Jan. 2, 2018, 12 pages.
Kuroda et al., "Trimethylsilyl Derivatives of Monomeric and Oligomeric Silicic Acids Extracted in Tetrahydrofuran", Journal of Inorganic and Nuclear Chemistry, vol. 42, No. 2, 1980, pp. 295-296.
Extended European Search Report in EP Application No. 15742622.2 dated Aug. 9, 2017, 10 pages.
Cella et al., "Procedures for the Preparation of Silanols", Journal of Organometallic Chemistry, 480, 1994, pp. 23-26.
Decision on Registration in KR Application No. 10-2016-7023558 dated May 21, 2018, 3 pages.
International Preliminary Report on Patentability and Written Opinion in International Application No. PCT/JP2015/052996 dated Aug. 9, 2016, 14 pages.

* cited by examiner

SILANOL COMPOUND, COMPOSITION, AND METHOD FOR PRODUCING SILANOL COMPOUND

TECHNICAL FIELD

The present invention relates to a silanol compound, a composition, and a method for producing a silanol compound, and more particularly to a silanol compound useful as, for example, a starting material for siloxane compounds that are used in a variety of fields such as automotive industry, construction industry, electronics, and pharmaceuticals.

BACKGROUND OF THE INVENTION

Because of their specific nature, siloxane compounds are very important compounds that are used in a variety of fields such as automotive industry, construction industry, electronics, and pharmaceuticals. In recent years, siloxane compounds have also become essential in the environmental and energy fields, for example, as sealing materials for LED and silane coupling agents for eco-tires, and it would not be an exaggeration to say that there is no field in which siloxane compounds are not used (market size as of 2009: 11.5 billion dollars, annual production volume: 1.23 million tons).

In general, the majority of siloxane compounds are synthesized via silanol compounds by hydrolysis, for example, by a sol-gel method using chlorosilane or an alkoxysilane as starting materials. Silanol compounds (inclusive of silane diols, silane triols, and silanetetraols), with the exception of some silane diols and silane triols having a bulky substituent group such as a phenyl group, are difficult to synthesize with a good yield because where water is present, condensation proceeds simultaneously with the hydrolysis. The silanol compounds are also known to have very low stability (stability in the presence of water) and condensate rapidly (NPL 2 and 3). For this reason, a large number of problems and limitations are associated with the silanol compounds, for example, (1) a large amount of reaction byproducts are formed; (2) the product structure is difficult to control; and (3) the silanol compounds cannot be adapted to reactions with substrates which are weak in water.

Accordingly, a method for synthesizing a silanol compound under anhydrous conditions or a method for synthesizing a siloxane compound not via a silanol compound are needed.

A method for treating silyl ether of pyrrolidine with n-BuLi to obtain a silanol compound is known as a method for synthesizing a silanol compound under anhydrous conditions (NPL 1). However, this method does not involve a reaction that is primarily aimed at the synthesis of a siloxane compound, and even when a siloxane compound is synthesized, the synthesis is difficult because the siloxane bonds are nucleophilically cleaved by n-BuLi.

Meanwhile, several methods based on cross coupling that uses a catalyst have been reported as methods for synthesizing a siloxane compound not via a silanol compound.

For example, Piers, Rubinsztajn, et al. have reported that siloxane bonds can be formed, while methane is being released, by reacting an alkoxysilane with hydrosilane in the presence of a $B(C_6F_5)_3$ catalyst (NPL 4 and 5). However, the problem associated with this reaction is that an exchange reaction of substituent groups proceeds between the substrates of starting materials and the reaction cannot be controlled due to $B(C_6F_5)_3$ which is a Lewis acid catalyst.

Bae et al. have recently reported that siloxane bonds can be formed, while methanole is being released, by reacting the following silanol compound and methoxysilane in the presence of a $Ba(OH)_2$ catalyst (NPL 6). However, this reaction can be adapted to only very few stable silanol compounds, and the method is hardly suitable for industrial production.

[C1]

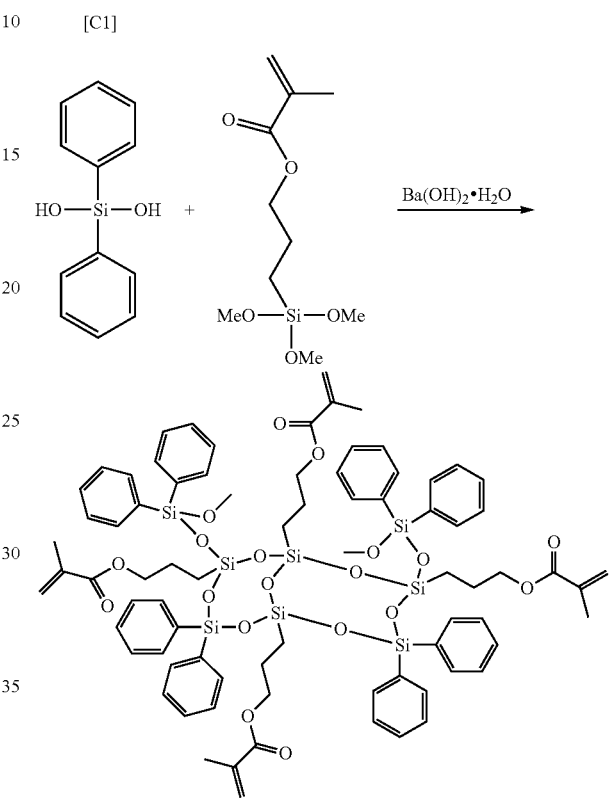

Further, Kuroda et al. have reported that siloxane bonds can be formed, while an alkyl chloride is being released, by reacting the following alkoxysilane with chlorosilane in the presence of a bismuth chloride catalyst (NPL 7). However, this reaction is restricted to very few substrates, and the method is hardly suitable for industrial production.

[C2]

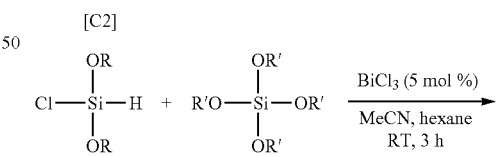

R = Me, Et    R' = $^t$Bu, $CHPh_2$

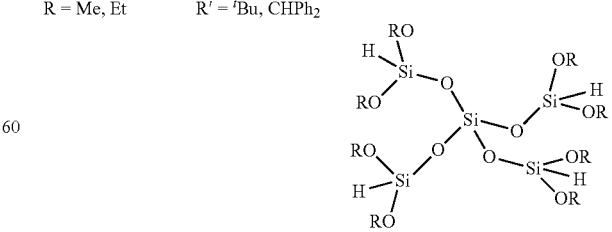

Further, the problem associated with the methods disclosed in NPL 4 to 7 is that since all those methods use homogeneous catalysts, the catalysts are difficult to remove from the reaction system after the reaction and they remain in the product obtained.

CITATION LIST

Non Patent Literature

[NPL 1] J. Am. Chem. Soc. 2000, 122, 408-409
[NPL 2] Fyfe, C. A; Aroca, P. P. J. Phys. Chem. B 1997, 101, 9504.
[NPL 3] Kim, Y; Jung, E. Chem. Lett. 2002, 992.
[NPL 4] Parks, D. J.; Blackwell, J. M.; Piers, W. E. J. Org. Chem. 2000, 65, 3090.
[NPL 5] Rubinsztajn, S.; Cella, J. A. Macromolecules 2005, 38, 1061.
[NPL 6] Synthetic Metals 2009, 159, 1288-1290
[NPL 7] Angew. Chem. Int. Ed. 2010, 49, 5273-5277

As mentioned hereinabove, silanol compounds, with the exception of some silane diols and silane triols having a bulky substituent group such as a phenyl group, are difficult to synthesize with a good yield because where water is present, condensation proceeds simultaneously with the hydrolysis. Further, since the produced silanol compounds rapidly condensate under the effect of impurities such as water, compositions in which such silanol compounds are stably compounded at a high concentration are difficult to obtain, and such silanol compounds are presently unsuitable as, for example, starting materials for siloxane compounds.

It is an objective of the present invention to provide a silanol compound and a composition thereof that can be used as a starting material for a siloxane compound, and also to provide a producing method suitable for producing a silanol compound with a good yield.

SUMMARY OF THE INVENTION

Based on the result of a comprehensive research aimed at the resolution of the abovementioned problems, the inventors have found that a composition including a specific amount of a specific silanol compound can actually be prepared, and that the composition is very advantageous as, for example, a starting material for a siloxane compound. This finding led to the creation of the present invention.

The present invention is disclosed hereinbelow.

<1> A composition comprising 5 mass % to 100 mass % of a silanol compound represented by the following Formulas (A) to (C):

[C3]

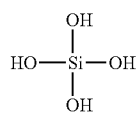

(A)

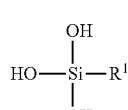

(B)

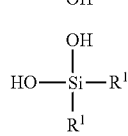

(C)

(in Formulas (B) and (C), $R^1$ are each, independently from each other, a hydrogen atom or a saturated hydrocarbon group with a carbon number of 1 to 10).

<2> The composition according to clause <1>, wherein the amount of the silanol compound represented by Formulas (A) to (C) is 10 mass % to less than 100 mass %.

<3> A silanol compound represented by the following Formula (D):

[C4]

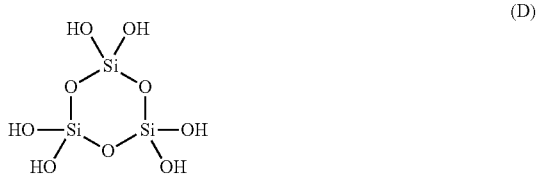 [SMILES: O[Si]1(O)O[Si](O)(O)O[Si](O)(O)O1]

(D)

<4> A composition comprising 5 mass % to less than 100 mass % of the silanol compound according to clause <3>.

<5> The composition according to any one of clauses <1>, <2>, and <4>, wherein the amount of water is 25 mass % or less.

<6> The composition according to any one of clauses <1>, <2>, <4>, and <5>, comprising more than 0 mass % and less than 95 mass % of at least one compound selected from the group consisting of an amine compound and an amide compound.

<7> The composition according to clause <6>, wherein the amide compound is tetramethylurea.

<8> The composition according to any one of clauses <1>, <2>, and <4> to <7>, comprising an ammonium salt, wherein a ratio of the ammonium salt to the silanol compound represented by the Formulas (A) to (C) [(total substance amount of the ammonium salt)/(total substance amount of the silanol compound)] is greater than 0 and equal to or less than 4.

<9> The composition according to any one of clauses <1>, <2>, and <4> to <8>, which is a solid body.

<10> A method for producing a silanol compound, comprising a hydrogenation step of conducting a reaction of a compound represented by the following Formula (1) with hydrogen in the presence of a catalyst, wherein the catalyst is a solid catalyst comprising a palladium (Pd) element and at least one element selected from the group consisting of platinum (Pt), ruthenium (Ru), rhodium (Rh), iridium (Ir), and gold (Au):

$$R^5{}_{4-n}Si(OCH_2Ar)_n \quad (1)$$

(In Formula (1), Ar represents an aromatic hydrocarbon group with a carbon number of 4 to 20 which may comprise at least one selected from the group consisting of a nitrogen atom, an oxygen atom, and a halogen atom; $R^5$ each represent, independently from each other, a hydrogen atom, a halogen atom, a hydroxyl group, or a hydrocarbon group with a carbon number of 1 to 20 which may comprise at least one selected from the group consisting of a nitrogen atom, an oxygen atom, and a halogen atom; and n represents an integer of 1 to 4. However, two or more R5 may be connected to each other to form a cyclic structure.)

<11> The method for producing a silanol compound according to clause <10>, wherein the hydrogenation step is a step of reacting the compound with hydrogen under anhydrous conditions.

<12> The method for producing a silanol compound according to clause <10> or <11>, wherein the hydrogenation step is a step of reacting the compound with hydrogen in the presence of an amine compound.

<13> The method for producing a silanol compound according to any one of clauses <10> to <12>, comprising an ammonium salt addition step of adding an ammonium salt to a product obtained in the hydrogenation step.

<14> The method for producing a silanol compound according to clause <13>, comprising a freeze drying step of freezing and exposing to a reduced pressure the product obtained in the ammonium salt addition step.

<15> The method for producing a silanol compound according to clause <13>, comprising a crystallization step of precipitating crystals by a poor solvent method from the product obtained in the ammonium salt addition step.

The present invention can provide a silanol compound and a composition thereof that can be used as, for example, a starting material for a siloxane compound.

DESCRIPTION OF THE EMBODIMENTS

Figure 1:
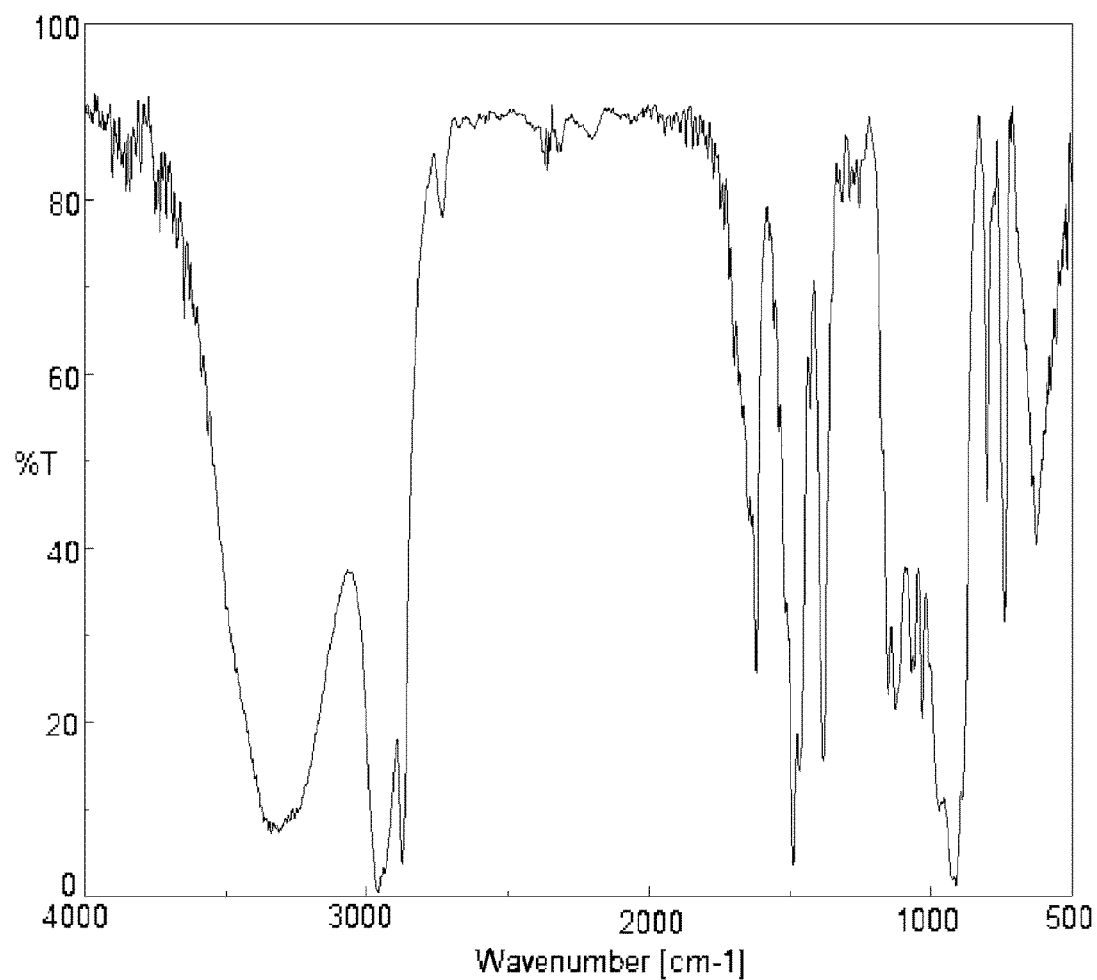
FIG. 1 is a measurement result of IR of the composition obtained in Example 67.

The present invention will be explained hereinbelow in greater detail with reference to specific examples thereof, but the present invention is not limited to the contents disclosed herein and can be implemented with appropriate changes, without departing from the essence of the invention.

<Composition>

The composition according to one aspect of the present invention (can be referred to hereinbelow simply as "composition of the present invention") is characterized by comprising 5 mass % or more to less than 100 mass % of a silanol compound represented by the following Formulas (A) to (C):

[C5]

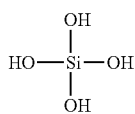
(A)

-continued

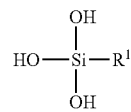
(B)

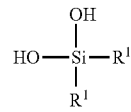
(C)

(in Formulas (B) and (C), $R^1$ are each, independently from each other, a hydrogen atom or a saturated hydrocarbon group with a carbon number of 1 to 10).

Based on the results of the research aimed at finding a silanol compound that can be used as, for example, a starting material for a siloxane compound, the inventors have found that a composition comprising 5 mass % or more to less than 100 mass % of a silanol compound represented by Formulas (A) to (C) can actually be prepared and that this composition is very advantageous as, for example, a starting material for a siloxane compound.

The silanol compounds represented by Formulas (A) to (C) are, in the order of description, a "silanetetraol", a "silane triol" having one saturated hydrocarbon group, and a "silane diol" having two saturated hydrocarbon groups. Where such silanol compound is synthesized by the conventional methods, condensation proceeds simultaneously with hydrolysis, and the compound is difficult to synthesize with a good yield. Further, since the produced silanol compound rapidly condensates under the effect of impurities such as water, compositions in which such silanol compound is stably compounded at a high concentration is difficult to obtain, and such compositions are presently unsuitable as, for example, starting materials for siloxane compounds.

The inventors have successfully prepared a composition comprising 5 mass % or more to less than 100 mass % of a silanol compound represented by Formulas (A) to (C) by producing the silanol compound under anhydrous conditions or producing the silanol compound in a solvent that acts to suppress the condensation of the silanol compound, and it was also clarified that since the silanol compound is stably present in the obtained composition, the composition can be used as, for example, a starting material for a siloxane compound.

The silanol compound represented by Formulas (A) to (C), which is to be comprised in the composition of the present invention, is not limited to one compound and means to be inclusive of two or more compounds corresponding to any of Formulas (A) to (C). Further, when two or more compounds are included, "comprising 5 mass % or more to less than 100 mass %" means the total amount of the silanol compounds represented by Formulas (A) to (C).

The composition of the present invention is characterized by comprising the silanol compound represented by Formulas (A) to (C), but specific examples of the silanol compound represented by the following Formula (B) and the silanol compound represented by the following Formula (C) are not particularly limited and can be selected, as appropriate, according to the objective.

[C6]

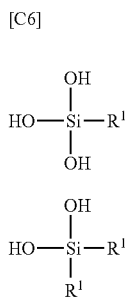

(In Formulas (B) and (C), $R^1$ represent each, independently from each other, a hydrogen atom or a saturated hydrocarbon group with a carbon number of 1 to 10.)

$R^1$ represent each, independently from each other, a hydrogen atom or a saturated hydrocarbon group with a carbon number of 1 to 10, but the "saturated hydrocarbon group" is not limited to a linear saturated hydrocarbon group and may have a branched or cyclic structure.

Examples of $R^1$ include a hydrogen atom (—H), a methyl group (-Me), an ethyl group (-Et), an n-propyl group (—$^n$Pr), an i-propyl group (—$^i$Pr), an n-butyl group (—$^n$Bu), a ti-butyl group (—$^t$Bu), an n-hexyl group (—$^n$Hex), and a cyclohexyl group, but the methyl group is particularly preferred.

Examples of the silanol compound represented by Formula (B) and the silanol compound represented by the Formula (C) include the compounds represented by the following formulas.

[C7]

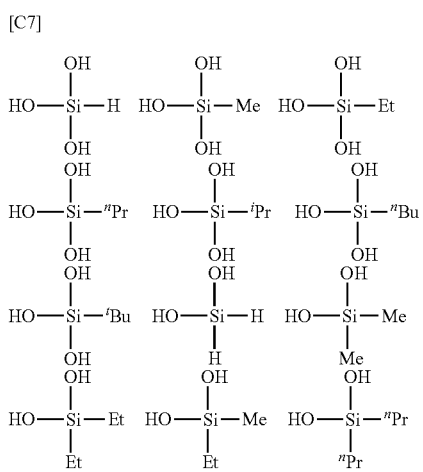

The composition of the present invention is characterized by comprising 5 mass % or more to less than 100 mass % of the silanol compound represented by Formulas (A) to (C), but the amount of the silanol compound (total amount when two or more silanol compounds are comprised) is preferably 10 mass % or more, more preferably 12 mass % or more, even more preferably 15 mass % or more, particularly preferably 18 mass % or more, and most preferably 20 mass % or more, and preferably 95 mass % or less, more preferably 80 mass % or less, and even more preferably 70 mass % or less. Within these ranges, the composition of the present invention can be readily used for various applications, and the composition of the present invention maintains good stability.

The composition of the present invention may comprise other compounds, provided that the silanol compound represented by Formulas (A) to (C) (can be referred to hereinbelow simply as "silanol compound") is comprised. Specific examples of such other compounds comprise water, oligomers (dimers, trimers, etc.) of the silanol compound represented by Formulas (A) to (C), amine compounds, amide compounds, and ammonium salt. These compounds will be explained hereinbelow in detail.

Since water promotes the condensation of the silanol compound and reduces the stability of the composition of the present invention, compounds with extremely small amount of water are preferred. The silanol compound can be used as a reactive agent of a cross-coupling reaction, for example, such as represented by the following reaction formula, but since the halogenated silane used for the reaction is unstable in water, compositions with a large amount of water are unsuitable for such reaction.

[C8]

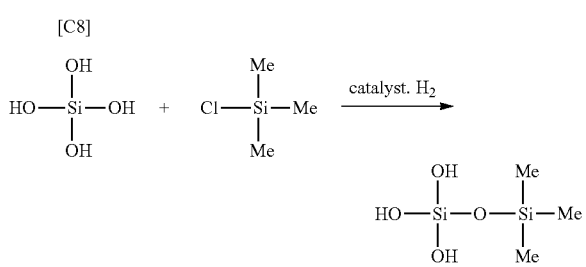

Further, the silanol compound can be used as a coating agent for forming a film of a siloxane compound, but where a composition with a large amount of water is used, the gas barrier ability of the formed film is degraded.

Water can be introduced from the atmosphere or generated by dehydration condensation of the silanol compound. Further, since water is used for hydrolysis of halogenated silanes or alkoxysilanes, water can be easily contained in the composition obtained by the producing method using such hydrolysis.

The amount of water in the composition of the present invention is usually 25 mass % or less, preferably 10 mass % or less, more preferably 5 mass % or less, even more preferably 1 mass % or less, particularly preferably 0.1 mass % or less, and most preferably 0.01 mass % or less. Within these ranges, the composition of the present invention can be readily used for various applications, and the composition of the present invention maintains good stability.

The oligomer of the silanol compound represented by Formulas (A) to (C) is a byproduct of, for example, the process for producing the silanol compound.

The compounds represented by the following formulas are examples of the oligomer of the silanol compound represented by Formulas (A) to (C). The composition may comprise one oligomer or two or more oligomers.

[C9]

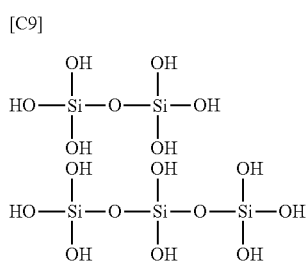

-continued

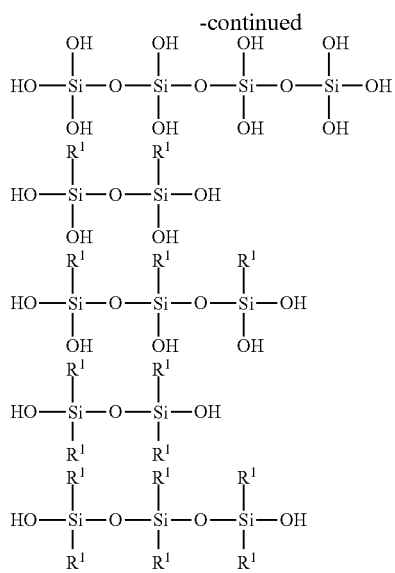

The amount of the oligomer (the total amount of the oligomers when two or more oligomers are comprised) of the silanol compound represented by Formulas (A) to (C) in the composition of the present invention is usually 30 mass % or less, preferably 20 mass % or less, more preferably 10 mass % or less, even more preferably 5 mass % or less, particularly preferably 1 mass % or less, and most preferably 0.1 mass % or less. Within these ranges, the composition of the present invention can be readily used for various applications, and the composition of the present invention maintains good stability.

The amine compounds are compounds that can be used in, for example, the process of producing the silanol compound. They are also compounds that suppress the hydrolysis and condensation of the silanol compound and effectively stabilize the composition of the present invention.

Specific types of amine compounds are not particularly limited (compounds having both an amino group and an amido group are classified into "amide compounds"), provided that they have an amino group (may be any of primary amines, secondary amines, and tertiary amines), and examples thereof include aniline ($NH_2Ph$), diphenylamine ($NHPh_2$), dimethylpyridine ($Me_2Pyr$), di-tert-butylpyridine ($^tBu_2Pyr$), pyrazine (Pyraz), triphenylamine ($NPh_3$), triethylamine ($Et_3N$), and di-isopropylethylamine ($^iPr_2EtN$). Among the amine compounds, aniline ($NH_2Ph$) is particularly preferred. The number of the amine compounds comprised in the composition is not limited to one, and two or more amine compounds may be comprised.

The amount of the amine compound (the total amount of the amine compounds when two or more thereof are comprised) in the composition of the present invention is preferably more than 0 mass %, more preferably 0.01 mass % or more, even more preferably 0.05 mass % or more, particularly preferably 0.10 mass % or more, and usually less than 95 mass %, preferably 50 mass % or less, more preferably 10 mass % or less, even more preferably 5 mass % or less, and particularly preferably 2.5 mass % or less. Within these ranges, the composition of the present invention can be readily used for various applications, and the composition of the present invention maintains good stability.

The amide compounds are compounds that can be used in, for example, the process of producing the silanol compound. They are also compounds that suppress the hydrolysis and condensation of the silanol compound and effectively stabilize the composition of the present invention.

Specific types of amide compounds are not particularly limited (compounds having both an amino group and an amido group are classified into "amide compounds"), provided that they have an amido bond, and examples thereof include tetramethylurea ($Me_4Urea$), N,N-dimethylformamide (DMF), N-methylacetamide, N,N-dimethylacetamide (DMAc), acetamide, and amide compounds represented by the following Formula (a). Among the amide compounds, tetramethylurea ($Me_4Urea$) is particularly preferred. The number of the amide compounds comprised in the composition is not limited to one, and two or more amide compounds may be comprised.

[C10]

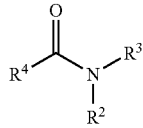

(a)

(In Formula (a), $R^2$ and $R^3$ each represent, independently from each other, a hydrogen atom or a hydrocarbon group with a carbon number of 1 to 3; $R^4$ represents a hydrocarbon group with a carbon number of 1 to 3.)

The amount of the amide compound (the total amount of the amide compounds when two or more thereof are comprised) in the composition of the present invention is preferably more than 0 mass %, more preferably 50 mass % or more, even more preferably 70 mass % or more, and usually less than 95 mass %, preferably 93 mass % or less, more preferably 90 mass % or less, even more preferably 85 mass % or less. Within these ranges, the composition of the present invention can be readily used for various applications, and the composition of the present invention maintains good stability.

When the amine compound and amide compound are comprised together, the total amount thereof is preferably more than 0 mass %, more preferably 50 mass % or more, and even more preferably 70 mass % or more, and usually less than 95 mass %, preferably 93 mass % or less, more preferably 90 mass % or less, and even more preferably 85 mass % or less. Within these ranges, the composition of the present invention can be readily used for various applications, and the composition of the present invention maintains good stability.

The ammonium salts suppress the hydrolysis and condensation of the silanol compound and effectively stabilize the composition of the present invention. They can be used as additives (stabilizing agents).

Specific types of the ammonium salts are not particularly limited, provided that they are configured by an ammonium ion and a counter anion. Examples of the ammonium ion include a tetrahydroammonium ion ($NH_4^+$), a tetramethylammonium ion ($NMe_4^+$), a tetrapropylammonium ion ($NPr_4^+$), a tetrabutylammonium ion ($NBu_4^+$), a benzyltributylammonium ion ($NBnBu_3^+$), a tributyl(methyl)ammonium ($NBu_3Me^+$) ion, a tetrapentylammonium ion ($NPen_4^+$), a tetrahexylammonium ion ($NHex_4^+$), a tetraheptylammonium ion ($NHep_4^+$), a 1-butyl-1-methylpyrrolidium ion ($BuMePyr^+$), a methyltrioctylammonium ion ($NMeOct_3^+$), and a dimethyldioctadecylammonium ion. Examples of the counter anion include a fluoride ion ($F^-$), a chloride ion (Cl⁻), a bromide ion (Br⁻), an iodide ion (I⁻), an acetoxy ion (AcO⁻), a nitrate ion (NO₃⁻), an azide ion (N₃⁻), a tetrafluoroboric acid ion (BF₄⁻), a perchloric acid ion (ClO₄⁻), and a sulfate ion (HSO₄⁻).

Tetrabutylammonium chloride (NBu₄Cl), tetrabutylammonium bromide (NBu₄Br), tetrapentylammonium chloride (NPen₄Cl), and dimethyldioctadecylammonium chloride are particularly preferred as the ammonium salt. One or two or more ammonium salts may be comprised in the composition.

The amount of the ammonium salt (the total amount of the ammonium salts when two or more thereof are comprised) in the composition of the present invention is preferably more than 0 mass %, and more preferably 50 mass % or more, and usually less than 95 mass % and preferably 80 mass % or less.

The ratio [(total substance amount of the ammonium salt)/(total substance amount of the silanol compound)] of the ammonium salt to the silanol compound in the composition of the present invention is preferably greater than 0 and more preferably 1 or more, and usually 4 or less, preferably 3 or less, and more preferably 2 or less.

Within these ranges, the composition of the present invention can be readily used for various applications, and the composition of the present invention maintains good stability.

The composition of the present invention may be in a liquid or solid state, but a solid state is preferred. In a solid state, the composition of the present invention can be readily used for various applications, and the composition of the present invention maintains good stability.

The application of the composition of the present invention is not particularly limited, and examples thereof include starting materials (reactants) for siloxane compounds, or the like, coating agents, resins, insulating films, gas barrier films, zeolites, mesoporous silica, fertilizers, pesticides, pharmaceuticals, and health goods.

A method for producing the composition of the present invention is not particularly limited, provided that the composition comprises 5 mass % or more to less than 100 mass % of the silanol compound represented by Formulas (A) to (C) above. The preferred producing method will be described hereinbelow in detail in <Method for Producing Silanol Compound>.

<Silanol Compound>

The silanol compound according to another aspect of the present invention (can be also referred to hereinbelow as "silanol compound of the present invention") is a compound represented by the following Formula (D).

[C11]

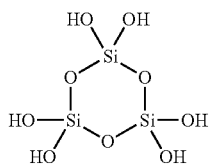

(D)

The silanol compound represented by Formula (D) is a cyclic trimer compound of silanetetraol (cyclic trisiloxanehexaol), and it was not reported that this compound could be obtained by the conventional methods.

The inventors have found that the silanol compound represented by Formula (D) can be prepared by using only an amide compound such as tetramethylurea (Me₄Urea) in a reaction in which a silanol compound is generated by the reaction of a benzyloxy-substituted silane and hydrogen. The detailed mechanism by which the silanol compound represented by Formula (D) is obtained has not been fully clarified, but the following explanation thereof can be suggested.

As mentioned hereinabove, amino compounds, amide compounds, and ammonium salts act to suppress the hydrolysis and condensation of silanol compounds. Among them, the action of amino compounds and ammonium salts is strong, whereas the action of amide compounds, when they are used alone, is apparently comparatively weak. For this reason, for example, where an amide compound is used as a solvent, and the reaction of a benzyloxy-substituted silane and hydrogen is conducted under conditions such that an amine compound, etc. is not comprised, a linear or cyclic trimer is formed by adequate condensation of the generated silanol compound, but subsequent condensation is suppressed, and the trimer is obtained as a product.

It has been mentioned hereinabove that the silanol compound of the present invention is advantageous as, for example, a starting material for a siloxane compound, but the silanol compound may be also used in a state of composition comprising also a compound other than the silanol compound. The amount of the silanol compound represented by Formula (D) in the composition is preferably 5 mass % or more, more preferably 10 mass % or more, even more preferably 20 mass % or more, particularly preferably 30 mass % or more, and most preferably 50 mass % or more, and also preferably 95 mass % or less. Within these ranges, the composition can be readily used as, for example, a starting material for a siloxane compound, and the composition maintains good stability.

Examples of compounds that can be comprised in the composition include water, amine compound, amide compound, and ammonium salts. Details relating to these compounds are herein omitted since they are the same as described hereinabove in the <Composition> section.

<Method for Producing Silanol Compound>

A method for producing a silanol compound which is yet another aspect of the present invention (can be also referred to hereinbelow simply as the "producing method of the present invention") comprises a hydrogenation step of conducting a reaction of a compound represented by the following Formula (1) with hydrogen in the presence of a catalyst (this step can be also referred to hereinbelow simply as the "hydrogenation step"), wherein the catalyst is a solid catalyst comprising a palladium (Pd) element and at least one element selected from the group consisting of platinum (Pt), ruthenium (Ru), rhodium (Rh), iridium (Ir), and gold (Au).

$$R^5_{4-n}Si(OCH_2Ar)_n \quad (1)$$

(In Formula (1), Ar represents an aromatic hydrocarbon group with a carbon number of 4 to 20 which may comprise at least one selected from the group consisting of a nitrogen atom, an oxygen atom, and a halogen atom; R⁵ each represent, independently from each other, a hydrogen atom, a halogen atom, a hydroxyl group, or a hydrocarbon group with a carbon number of 1 to 20 which may comprise at least one selected from the group consisting of a nitrogen atom, an oxygen atom, and a halogen atom; and n represents an integer of 1 to 4. However, two or more R5 may be connected to each other to form a cyclic structure.)

As mentioned hereinabove, where a silanol compound is synthesized by the conventional method, condensation proceeds simultaneously with hydrolysis. For this reason, the silanol compound is difficult to synthesize with a good yield. The inventors have found that a silanol compound can be produced with a yield higher than that obtained, for example, by using a solid catalyst comprising only palladium (Pd) (inclusive of catalyst in which Pd is supported on a catalyst support), by using a solid catalyst in which a palladium (Pd) element is combined with a hydrogenatable metal element such as platinum (Pt) in a method for synthesizing a silanol compound by reacting a benzyloxy-substituted silane represented by Formula (1) with hydrogen.

A method for synthesizing a silanol compound by reacting a benzyloxy-substituted silane with hydrogen can be represented, for example, by the following Reaction Formula (2).

[C12]

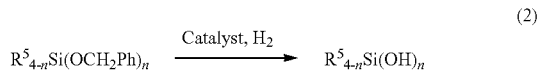

(2)

The "silanol compound" in the producing method of the present invention means a compound having a Si—OH structure that is formed by a reaction of the compound represented by Formula (1) with hydrogen, and also means that the number of hydroxyl groups (—OH) bonded to the silicon atom in this compound is not particularly limited. Thus, the "silanol compound" is meant to be inclusive of silane monools (SiRR'R"OH), silane diols (SiRR'(OH)$_2$), silane triols (SiR(OH)$_3$), and silanetetraol (Si(OH)$_4$).

Further, the "solid catalyst" means that the state of palladium (Pd), etc., is not particularly limited, provided that the solid catalyst comprises palladium (Pd), platinum (Pt), etc., as a constituent component and is solid at room temperature. Thus, in the "solid catalyst", palladium (Pd) may be in a state of palladium (II) oxide, a state in which the surface is oxidized and the interior is metallic palladium, or in the form of an alloy with platinum or the like.

The hydrogenation step is a step in which the compound represented by the following Formula (1) is reacted with hydrogen in the presence of a catalyst, but the compound represented by Formula (1) is not particularly limited and can be selected, as appropriate, according to the objective.

(1)

(In Formula (1), Ar represents an aromatic hydrocarbon group with a carbon number of 4 to 20 which may comprise at least one selected from the group consisting of a nitrogen atom, an oxygen atom, and a halogen atom; $R^5$ each represent, independently from each other, a hydrogen atom, a halogen atom, a hydroxyl group, or a hydrocarbon group with a carbon number of 1 to 20 which may comprise at least one selected from the group consisting of a nitrogen atom, an oxygen atom, and a halogen atom; and n represents an integer of 1 to 4. However, two or more $R^5$ may be connected to each other to form a cyclic structure.)

Ar in Formula (1) represents an aromatic hydrocarbon group with a carbon number of 4 to 20 which may comprise at least one selected from the group consisting of a nitrogen atom, an oxygen atom, and a halogen atom. The "aromatic hydrocarbon group" means to be inclusive of monocyclic aromatic hydrocarbon groups having aromaticity, such as a phenyl group, and also of polycyclic aromatic hydrocarbon groups having aromaticity, such as a naphthyl group. Further, "may comprise at least one selected from the group consisting of a nitrogen atom, an oxygen atom, and a halogen atom" means that the aromatic hydrocarbon group may comprise a functional group comprising a nitrogen atom, an oxygen atom, or a halogen atom, such as an amino group (—NH$_2$), a nitro group (—NO$_2$), and a fluoro group (—F), and also means that a linking group comprising a nitrogen atom, an oxygen atom, or a halogen atom, such as an ether group (—O—) and an imino group (—NH—) may be comprised inside or at an end of the carbon skeleton. Therefore, the aromatic hydrocarbon group which "may comprise at least one selected from the group consisting of a nitrogen atom, an oxygen atom, and a halogen atom" is inclusive, for example, of aromatic hydrocarbon groups with a carbon number of 6 which comprise a nitro group, such as a nitrophenyl group, and also of heterocyclic structures with a carbon number of 5 which comprise a nitrogen atom inside a carbon skeleton, such as a pyridyl group.

The carbon number of the aromatic hydrocarbon group is preferably 6 or more, usually 18 or less, preferably 14 or less.

When the aromatic hydrocarbon group comprises a functional group, the functional group may be an amino group (—NH$_2$), a nitro group (—NO$_2$), a methoxy group (—OMe), an ethoxy group (—OEt), a fluoro group (—F), a chloro group (—Cl), a bromo group (—Br), an iodo group (—I), and a trifluoromethyl group (—CF$_3$).

Specific examples of the aromatic hydrocarbon group include a phenyl group (-Ph), a naphthyl group (—C$_{10}$H$_7$), an aminophenyl group (-PhNH$_2$), a nitrophenyl group (-PhNO$_2$), a methoxyphenyl group (-PhOMe), an ethoxyphenyl group (-PhOEt), a fluorophenyl group (-PhF), and a difluorophenyl group (-PhF$_2$).

$R^5$ each represent, independently from each other, a hydrogen atom, a halogen atom, a hydroxyl group, or a hydrocarbon group with a carbon number of 1 to 20 which may comprise at least one selected from the group consisting of a nitrogen atom, an oxygen atom, and a halogen atom.

The "hydrocarbon group" is not limited to linear saturated hydrocarbon groups and may have a carbon-carbon unsaturated bond, a branched structure, or a cyclic structure. The meaning of "may comprise at least one selected from the group consisting of a nitrogen atom, an oxygen atom, and a halogen atom" is the same as in the above-described case relating to Ar. Therefore, the hydrocarbon group which "may comprise at least one selected from the group consisting of a nitrogen atom, an oxygen atom, and a halogen atom" is inclusive, for example, of hydrocarbon groups with a carbon number of 2 which comprise an oxygen atom inside a carbon skeleton, such as —CH$_2$—O—CH$_3$, and hydrocarbon groups with a carbon number of 2 which comprise an oxygen atom at the end of the carbon skeleton, such as —O—CH$_2$—CH$_3$ (ethoxy group).

When $R^5$ is a hydrocarbon group, the carbon number is preferably 18 or less and more preferably 16 or less.

When the hydrocarbon group comprises a functional group, the functional group may be an amino group (—NH$_2$), a nitro group (—NO$_2$), a methoxy group (—OMe), an ethoxy group (—OEt), a fluoro group (—F), a chloro group (—Cl), a bromo group (—Br), an iodo group (—I), a trifluoromethyl group (—CF$_3$), etc.

Examples of $R^5$ include a hydrogen atom, a halogen atom, a hydroxyl group, an alkyl group with a carbon number of 1 to 20, an alkoxy group with a carbon number of 1 to 20, a cycloalkyl group with a carbon number of 3 to 20, an aryl group with a carbon number of 6 to 20, an aralkyl group with a carbon number of 7 to 16, an acyl group with a carbon number of 1 to 19, and an acyloxy group with a carbon number of 1 to 19.

Specific examples of the compound represented by Formula (1) include tetrabenzyloxysilane, tribenzyloxysilane, methyltribenzyloxysilane, phenyltribenzyloxysilane, ethyltribenzyloxysilane, cyclohexyltribenzyloxysilane, methoxytribenzyloxysilane, ethoxytribenzyloxysilane, phenoxytribenzyloxysilane, t-butoxytribenzyloxysilane, cyclohexyloxytribenzyloxysilane, dibenzyloxysilane, methyldibenzyloxysilane, phenyldibenzyloxysilane, ethyldibenzyloxysilane, methoxydibenzyloxysilane, ethoxydibenzyloxysilane, phenoxydibenzyloxysilane, t-butoxydibenzyloxysilane, cyclohexyloxydibenzyloxysilane, dimethyldibenzyloxysilane, diphenyldibenzyloxysilane, diethyldibenzyloxysilane, dimethoxydibenzyloxysilane, diethoxydibenzyloxysilane, diphenoxydibenzyloxysilane, di-t-butoxydibenzyloxysilane, dicyclohexyloxydibenzyloxysilane, methylphenyldibenzyloxysilane, methylethyldibenzyloxysilane, phenyldibenzyloxysilane, ethyldibenzyloxysilane, methoxydibenzyloxysilane, ethoxydibenzyloxysilane, phenoxydibenzyloxysilane, t-butoxydibenzyloxysilane, cyclohexyloxydibenzyloxysilane, dimethyldibenzyloxysilane, diphenyldibenzyloxysilane, diethyldibenzyloxysilane, dicyclohexyldibenzyloxysilane, dimethoxydibenzyloxysilane, diethoxydibenzyloxysilane, diphenoxydibenzyloxysilane, di-t-butoxydibenzyloxysilane, dicyclohexyloxydibenzyloxysilane, methylbenzyloxysilane, phenylbenzyloxysilane, ethylbenzyloxysilane, methoxybenzyloxysilane, ethoxybenzyloxysilane, phenoxybenzyloxysilane, t-butoxybenzyloxysilane, cyclohexyloxybenzyloxysilane, dimethylbenzyloxysilane, diphenylbenzyloxysilane, diethylbenzyloxysilane, dimethoxybenzyloxysilane, diethoxybenzyloxysilane, diphenoxybenzyloxysilane, di-t-butoxybenzyloxysilane, dicyclohexyloxybenzyloxysilane, methylphenylbenzyloxysilane, methylethylbenzyloxysilane, trimethylbenzyloxysilane, triphenylbenzyloxysilane, triethylbenzyloxysilane, trimethoxybenzyloxysilane, triethoxybenzyloxysilane, triphenoxybenzyloxysilane, tri-t-butoxybenzyloxysilane, tricyclohexyloxybenzyloxysilane, and t-butyldimethylsilylbenzyloxysilane.

The hydrogenation step is characterized by that the catalyst is a solid catalyst comprising a palladium (Pd) element and at least one element selected from the group consisting of platinum (Pt), ruthenium (Ru), rhodium (Rh), iridium (Ir), and gold (Au), but the specific material form of the solid catalyst is not particularly limited. For example, palladium and platinum may be supported on a catalyst support, palladium may be supported on metallic platinum particles, or a mixture of metallic palladium particles and metallic platinum particles may be used. Among them, a catalyst supported on a catalyst support is preferred because of a high specific surface area.

Well-known materials suitable for catalyst supports can be used, as appropriate, for the catalyst support, specific examples thereof comprising carbon materials such as active carbon, graphite carbon, and acetylene black, and metal oxides such as silicon oxide, aluminum oxide, silica-alumina, chromium oxide, cerium oxide, titanium oxide, and zirconium oxide. Because of a high specific surface area, it is preferred that carbon materials such as active carbon be used as the catalyst support. It is more preferred that the catalyst support be a porous material.

The combination of palladium (Pd) element and another element such as platinum (Pt) in the solid catalyst is not particularly limited and can be selected, as appropriate, according to the objective, examples of suitable combinations including: palladium (Pd) element and platinum (Pt) element, palladium (Pd) element and ruthenium (Ru) element, palladium (Pd) element and rhodium (Rh), palladium (Pd) element and iridium (Ir), palladium (Pd) element and gold (Au), palladium (Pd) element and platinum (Pt) element and ruthenium (Ru), and palladium (Pd) element and platinum (Pt) element and rhodium (Rh). Among them, the combination of palladium (Pd) element and platinum (Pt) element is particularly preferred because the silanol compound can be produced with a good yield.

When the solid catalyst comprises platinum (Pt) element, the ratio (mass ratio) of platinum (Pt) element to palladium (Pd) element is usually 0.0001 or more, preferably 0.001 or more, and more preferably 0.01 or more, and usually 1 or less, preferably 0.25 or less, and more preferably 0.15 or less.

When the solid catalyst comprises ruthenium (Ru) element, the ratio (mass ratio) of ruthenium (Ru) element to palladium (Pd) element is usually 0.0001 or more, preferably 0.001 or more, and more preferably 0.01 or more, and usually 1 or less, preferably 0.25 or less, and more preferably 0.15 or less.

When the solid catalyst comprises rhodium (Rh) element, the ratio (mass ratio) of rhodium (Rh) element to palladium (Pd) element is usually 0.0001 or more, preferably 0.001 or more, and more preferably 0.01 or more, and usually 1 or less, preferably 0.25 or less, and more preferably 0.15 or less.

When the solid catalyst comprises iridium (Ir) element, the ratio (mass ratio) of iridium (Ir) element to palladium (Pd) element is usually 0.0001 or more, preferably 0.001 or more, and more preferably 0.01 or more, and usually 1 or less, preferably 0.25 or less, and more preferably 0.15 or less.

When the solid catalyst comprises gold (Au) element, the ratio (mass ratio) of gold (Au) element to palladium (Pd) element is usually 0.0001 or more, preferably 0.001 or more, and more preferably 0.01 or more, and usually 1 or less, preferably 0.25 or less, and more preferably 0.15 or less.

Within these ranges, the silanol compound can be produced with a good yield.

The amount of palladium (Pd) element, etc. in the solid catalyst is not particularly limited and can be selected, as appropriate, according to the objective. However, when the solid catalyst is a catalyst that is supported on a carbon material (catalyst support), the amount of palladium (Pd) element is usually 0.01 mass % or more, preferably 0.1 mass % or more, and more preferably 1 mass % or more, and usually 50 mass % or less, preferably 30 mass % or less, and more preferably 20 mass % or less.

When the solid catalyst comprises platinum (Pt) element and the catalyst in the solid catalyst is supported on a carbon material (catalyst support), the amount of platinum (Pt) element is usually 0.01 mass % or more, preferably 0.1 mass % or more, and more preferably 1 mass % or more, and usually 50 mass % or less, preferably 30 mass % or less, and more preferably 20 mass % or less.

When the solid catalyst comprises ruthenium (Ru) element and the catalyst in the solid catalyst is supported on a carbon material (catalyst support), the amount of ruthenium (Ru) element is usually 0.01 mass % or more, preferably 0.1 mass % or more, and more preferably 1 mass % or more, and usually 50 mass % or less, preferably 30 mass % or less, and more preferably 20 mass % or less.

When the solid catalyst comprises rhodium (Rh) element and the catalyst in the solid catalyst is supported on a carbon material (catalyst support), the amount of rhodium (Rh)

element is usually 0.01 mass % or more, preferably 0.1 mass % or more, and more preferably 1 mass % or more, and usually 50 mass % or less, preferably 30 mass % or less, and more preferably 20 mass % or less.

When the solid catalyst comprises iridium (Ir) element and the catalyst in the solid catalyst is supported on a carbon material (catalyst support), the amount of iridium (Ir) element is usually 0.01 mass % or more, preferably 0.1 mass % or more, and more preferably 1 mass % or more, and usually 50 mass % or less, preferably 30 mass % or less, and more preferably 20 mass % or less.

When the solid catalyst comprises gold (Au) element and the catalyst in the solid catalyst is supported on a carbon material (catalyst support), the amount of gold (Au) element is usually 0.01 mass % or more, preferably 0.1 mass % or more, and more preferably 1 mass % or more, and usually 50 mass % or less, preferably 30 mass % or less, and more preferably 20 mass % or less.

A commercial or self-prepared solid catalysts may be used. ASCA-2 (Pd 4.5 mass %, Pt 0.5 mass %) produced by N.E. Chemcat Corporation is an example of the commercial solid catalyst.

A well-known method can be used, as appropriate, to prepare the solid catalyst. For example, when palladium and platinum are supported on a catalyst support, a method of impregnating the catalyst support with a palladium salt and then impregnating with a platinum salt and a method of co-precipitating a palladium salt and a platinum salt on the catalyst support can be used. Examples of starting materials to be used for preparing the solid catalyst comprise chlorides, hydrochlorides, nitrates, sulfates, organic acid salts, ammine salts, alkali salts, and organic complexes of palladium (Pd), etc. Thus, divalent palladium chloride, sodium chloropalladate, potassium chloroplalladate, palladium nitrate, and palladium acetate are examples of palladium (Pd) sources; chloroplatinic acid and potassium chloroplatinate are examples of platinum (Pt) sources; ruthenium chloride and ruthenium nitrate are examples of ruthenium (Ru) sources; rhodium chloride and rhodium sulfate are examples of rhodium (Rh) sources; iridium sulfate and chloroiridic acid are examples of iridium (Ir) sources; and chloroauric acid, gold sodium sulfite, and gold acetate are examples of gold (Au) sources.

The amount of the solid catalyst to be used in the hydrogenation step is not particularly limited and can be selected, as appropriate, according to the objective. When represented as the total amount (substance amount) of palladium (Pd) element, the amount of the solid catalyst, calculated based on benzyloxy groups, is usually 0.1 mol % or more, preferably 0.5 mol % or more, and more preferably 1.0 mol % or more, and usually 15.0 mol % or less, preferably 10.0 mol % or less, and more preferably 5.0 mol % or less. Within these ranges, the silanol compound can be produced with a good yield.

Provided that the compound represented by Formula (1) is reacted with hydrogen in the presence of a catalyst, other conditions of the hydrogenation step are not particularly limited, but it is preferred that the reaction between the compound represented by Formula (1) and hydrogen be conducted under anhydrous conditions.

The "anhydrous conditions", as referred to herein, mean that starting materials or reaction are controlled such that the amount of moisture in the reaction system is reduced to a minimum, for example, by not using water or a compound comprising moisture as a starting material or by conducting the reaction such that moisture contained in the atmosphere is not admixed. Therefore, for example, water is sometimes generated by the condensation of the generated silanol compound, but the "anhydrous conditions" do not mean ideal anhydrous conditions under which such water is also not comprised, and mean that the specific concentration, etc. of water comprised in the reaction system is also not particularly limited.

It is preferred that the reaction between the compound represented by Formula (1) and hydrogen in the hydrogenation step be conducted by using a solvent.

Examples of suitable solvents include aliphatic hydrocarbon compounds such as n-hexane, n-heptane, and n-octane; aromatic hydrocarbon compounds such as benzene, toluene, and xylene; alicyclic hydrocarbon compounds such as cyclohexane and decalin; alcohol compounds such as methanol, ethanol, n-propanol, and i-propanol; ether compounds such as tetrahydrofuran (THF), tetrahydropyran, dioxane, diethyl ether, dimethyl ether, diisopropyl ether, diphenyl ether, and methyl ethyl ether; ester compounds such as ethyl acetate, n-amyl acetate, and ethyl lactate; halogenated hydrocarbon compounds such as methylene chloride, chloroform, carbon tetrachloride, tetrachloroethane, and hexachloroethane; amide compounds such as N,N-dimethylformamide (DMF), N-methylacetamide, N,N-dimethylacetamide (DMAc), and acetamide; and aprotic polar solvents such as acetone, methyl ethyl ketone, phenyl methyl ketone, and dimethyl sulfoxide (DMSO). These reaction solvents may be a mixture of two or more thereof.

Among them, amide compounds (a compound comprising both an amino group and an amido group are assumed to be classified into "amide compounds") such as tetramethylurea (Me$_4$Urea), N,N-dimethylformamide (DMF), N-methylacetamide, N,N-dimethylacetamide (DMAc), acetamide, and compounds represented by the following Formula (a) are preferred because the silanol compound can be produced with a good yield, and tetramethylurea (Me$_4$Urea) is particularly preferred.

[C13]

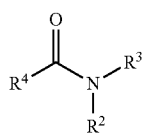

(a)

(In Formula (a), $R^2$ and $R^3$ each represent, independently from each other, a hydrogen atom or a hydrocarbon group with a carbon number of 1 to 3; $R^4$ represents a hydrocarbon group with a carbon number of 1 to 3.)

Where a solvent comprising such an amide compound is used, the silanol compound is stabilized by forming a hydrogen bond with the amide compound. Therefore, the silanol compound can be produced with a good yield.

It is preferred that the reaction between the compound represented by Formula (1) and hydrogen in the hydrogenation step be conducted in the presence of an amine compound. "In the presence of an amine compound", as referred to herein, means that the amine compound is added to a solution comprising, for example, the compound represented by Formula (1) and the solvent. Where the reaction is conducted in the presence of an amine compound, an acid generated when hydrogen is caused to act upon the catalyst is neutralized and hydrolysis of the silanol compound is suppressed. As a result, the silanol compound can be produced with a good yield. The specific type of the "amine compound" (a compound comprising both an amino group and an amido group are assumed to be classified into "amide compounds") is not particularly limited, provided that the compound has an amino group (may be primary amine, secondary amine, or tertiary amine), and examples thereof include aniline ($NH_2Ph$), diphenylamine ($NHPh_2$), dimethylpyridine ($Me_2Pyr$), di-tert-butylpyridine ($^tBu_2Pyr$), pyrazine (Pyraz), triphenylamine ($NPh_3$), triethylamine ($Et_3N$), and di-isopropylethylamine ($^iPr_2EtN$). Among the amine compounds, aniline ($NH_2Ph$) is particularly preferred. The number of the amine compounds comprised in the composition is not limited to one and two or more amine compounds may be comprised.

The added amount of the amine compound (substance amount) is not particularly limited and can be selected, as appropriate, according to the objective. When calculated based on benzyloxy groups, this amount is usually 0.0001-fold or greater, preferably 0.001-fold or greater, and more preferably 0.01-fold or greater, and usually 10.0-fold or less, preferably 2.0-fold or less, and more preferably 1.0-fold or less.

The amount of the amine compound (substance amount) added to produce a silanol compound monomer, such as the silanol compound represented by Formula (A), when calculated based on benzyloxy groups, is usually 0.0001-fold or greater, preferably 0.001-fold or greater, and more preferably 0.01-fold or greater, and usually 0.5-fold or less, preferably 0.10-fold or less, and more preferably 0.05-fold or less. Within these ranges, the silanol compound, etc. represented by Formula (A) can be produced with a more favorable yield.

[C14]

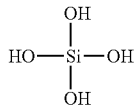

(A)

Meanwhile, the amount of the amine compound (substance amount) added to produce the silanol compound represented by Formula (D), when calculated based on benzyloxy groups, is usually 0-fold or greater, preferably 0.001-fold or greater, and more preferably 0.01-fold or greater, and usually 0.5-fold or less, preferably 0.10-fold or less, more preferably 0.05-fold or less. Within these ranges, the silanol compound represented by Formula (D) can be produced with a more favorable yield.

[C15]

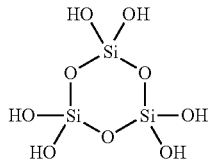

(D)

The temperature condition of the hydrogenation step is usually −80° C. or higher, preferably −20° C. or higher, and more preferably 0° C. or higher, and usually 250° C. or lower, preferably 100° C. or lower, and more preferably 80° C. or lower.

Hydrogen in the hydrogenation step is usually present in a gas phase as a hydrogen gas. The hydrogen pressure (partial hydrogen pressure) is usually 0.01 atm or higher, preferably 0.1 atm or higher, and more preferably 1 atm or higher, and usually 100 atm or lower, preferably 10 atm or lower, and more preferably 5 atm or lower.

The reaction time in the hydrogenation step is usually 0.1 h or more, preferably 0.5 h or more, and more preferably 1.0 h or more, and usually 24 h or less, preferably 12 h or less, and more preferably 6 h or less.

Within these ranges the silanol compound can be produced with a good yield.

The specific operation procedure for conducting the reaction of the compound represented by Formula (1) with hydrogen in the hydrogenation step is not particularly limited, and a well-known procedure can be used as appropriate. Usually, the solid catalyst and the compound represented by Formula (1) are loaded into a reaction vessel and mixed (the solvent and amine compound may be also comprised), the atmosphere inside the reaction vessel is then replaced with hydrogen gas, and the reaction is performed. Upon completion of the reaction, the solid catalysts can be separated by centrifugal separation or with a filter, or the silanol compound can be taken out after filtration with Celite or Hyflo Super-Cel.

Provided that the producing method of the present invention comprises the above-described hydrogenation step, the method is not otherwise particularly limited. For example, the method may also comprise an ammonium salt addition step of adding an ammonium salt to the product obtained in the hydrogenation step (can be simply referred to hereinbelow as "ammonium salt addition step"), a freeze drying step of freezing and exposing to a reduced pressure the product obtained in the ammonium salt addition step (can be simply referred to hereinbelow as "freeze drying step"), and a crystallization step of precipitating crystals by a poor solvent method from the product obtained in the ammonium salt addition step (can be simply referred to hereinbelow as "crystallization step"). The ammonium salt addition step, freeze drying step, crystallization step will be explained hereinbelow in greater detail.

In the ammonium salt addition step, an ammonium salt is added to the product obtained in the above-described hydrogenation step. The specific types and amount added of the ammonium salt are the same as described in the "Composition" section, and the explanation thereof is herein omitted. As mentioned hereinabove, the effect of the ammonium salt is in the suppression of hydrolysis and condensation of the silanol compound and in the stabilization thereof.

In the freeze drying step, the product obtained in the ammonium salt addition step is frozen and exposed to a reduced pressure. Specific freeze drying conditions are not particularly limited, and well-known conditions can be selected as appropriate. Further, the solvent and amine compound, etc. used in the hydrogenation step can be removed in the freeze drying step.

The temperature conditions for freezing in the freeze drying step are not particularly limited, provided that the product obtained in the ammonium salt addition step is frozen. The temperature is usually 10° C. or lower, preferably 0° C. or lower, and more preferably −20° C. or lower, and usually −196° C. or higher, preferably −150° C. or higher, and more preferably −100° C. or higher.

The temperature during drying in the freeze drying step is usually 10° C. or lower, preferably 0° C. or lower, and more preferably −20° C. or lower, and usually −196° C. or higher, preferably −150° C. or higher, and more preferably −100° C. or higher.

The pressure in the freeze drying step is usually 100 Pa or lower, preferably 20 Pa or lower, and more preferably 3 Pa or lower, and usually $10^{-5}$ Pa or higher, preferably 0.01 Pa or higher, and more preferably 1 Pa or higher.

The drying time in the freeze drying step is usually 100 h or less, preferably 50 h or less, and more preferably 10 h or less, and usually 1 h or more, preferably 5 h or more, and more preferably 10 h or more.

In the crystallization step, crystals are precipitated by a poor solvent method from the product obtained in the above-described ammonium salt addition step. Specific conditions of the poor solvent method are not particularly limited, and well-known conditions can be selected as appropriate. With the crystallization step, the composition comprising the silanol compound is precipitated as crystals. Therefore, the solvent and amine compound, etc. used in the hydrogenation step are easily separated.

The boiling point of the solvent to be used in the crystallization step is usually 0° C. or higher, preferably 10° C. or higher, and more preferably 30° C. or higher, and usually 300° C. or lower, preferably 200° C. or lower, and more preferably 100° C. or lower.

Examples of the solvent to be used in the crystallization step include diethyl ether ($Et_2O$), N,N-dimethylacetamide, N,N-dimethylformamide, N-methylacetamide, dimethyl sulfoxide (DMSO), and tetramethylurea.

The crystallization time (stationary time) is usually 720 h or less, preferably 240 h or less, and more preferably 50 h or less, and usually 1 h or more, preferably 5 h or more, and more preferably 10 h or more.

EXAMPLES

The present invention will be explained hereinbelow in greater detail with reference to examples and comparative examples thereof, but appropriate changes can be made without departing from the essence of the present invention. Therefore, the scope of the invention should not be interpreted as being limited by the specific examples described below.

[Synthesis of Silanol Compound Precursors]

Synthesis Example 1: Synthesis of methyltribenzyloxysilane ($MeSi(OBn)_3$)

Benzyl alcohol (66.0 g, 610.3 mmol), triethylamine (61.7 g, 609.7 mmol), and dimethylaminopyridine (244.3 mg, 2.00 mmol) were placed into a two-neck flask equipped with a magnetic stirrer, followed by dilution with 500 ml of dichloromethane. The system was cooled to 0° C., and methyltrichlorosilane (29.9 g, 200.0 mmol) was dropwise added over 3 h. After the dropwise addition, stirring was conducted for 12 h at room temperature, dichloromethane was distilled off and fractionating as a hexane solution was conducted, and methyltribenzyloxysilane, which was a precursor, was obtained at a yield of 84% (61.2 g).

Synthesis Example 2: Synthesis of phenyltribenzyloxysilane ($PhSi(OBn)_3$)

Benzyl alcohol (3.14 g, 29.0 mmol), triethylamine (2.97 g, 29.3 mmol), and dimethylaminopyridine (139 mg, 1.14 mmol) were placed into a two-neck flask equipped with a magnetic stirrer, followed by dilution with 10 ml of dichloromethane. The system was cooled to 00° C., and a solution obtained by diluting phenyltrichlorosilane (2.00 g, 9.45 mmol) with 10 ml of dichloromethane was dropwise added over 10 min. After the dropwise addition, stirring was conducted for 12 h at room temperature, dichloromethane was distilled off, and fractionating as a hexane solution was conducted, thereby providing phenyltribenzyloxysilane at a yield of 73% (2.94 g).

Synthesis Example 3: Synthesis of dimethyldibenzyloxysilane ($Me_2Si(OBn)_2$)

Benzyl alcohol (66.5 g, 614.9 mmol), triethylamine (62.2 g, 614.7 mmol), and dimethylaminopyridine (183.3 mg, 1.50 mmol) were placed into a two-neck flask equipped with a magnetic stirrer, followed by dilution with 500 ml of dichloromethane. The system was cooled to 00° C., and a solution obtained by diluting dimethyldichlorosilane (38.7 g, 299.9 mmol) with dichloromethane was dropwise added over 4 h. After the dropwise addition, stirring was conducted for 12 h at room temperature, dichloromethane was distilled off and fractionated as a hexane solution, and dimethyldibenzyloxysilane, which was a precursor, was obtained at a yield of 80% (65.6 g).

Synthesis Example 4: Synthesis of diphenyldibenzyloxysilane ($Ph_2Si(OBn)_2$)

Benzyl alcohol (4.5 g, 41.6 mmol), triethylamine (4.3 g, 42.5 mmol), and dimethylaminopyridine (24.4 mg, 0.20 mmol) were placed into a two-neck flask equipped with a magnetic stirrer, followed by dilution with 80 ml of dichloromethane. The system was cooled to 00° C., and diphenyldichlorosilane (5.1 g, 20.1 mmol) was dropwise added over 3 h. After the dropwise addition, stirring was conducted for 12 h at room temperature, dichloromethane was distilled off and fractionated as a hexane solution, and diphenyldibenzyloxysilane, which was a precursor, was obtained at a yield of 84% (6.7 g).

Synthesis Example 5: Synthesis of trimethylbenzyloxysilane ($Me_3Si(OBn)$)

Benzyl alcohol (6.8 g, 62.9 mmol), triethylamine (6.4 g, 63.2 mmol), and dimethylaminopyridine (73.3 mg, 0.60 mmol) were placed into a two-neck flask equipped with a magnetic stirrer, followed by dilution with dichloromethane. The system was cooled to 00° C., and trimethylchlorosilane (6.5 g, 59.8 mmol) was dropwise added over 2 h. After the dropwise addition, stirring was conducted for 12 h at room temperature, dichloromethane was distilled off and fractionated as a hexane solution, and trimethylbenzyloxysilane, which was a precursor, was obtained at a yield of 81% (8.7 g).

Synthesis Example 6: Synthesis of triphenylbenzyloxysilane ($Ph_3Si(OBn)$)

Benzyl alcohol (2.3 g, 21.3 mmol), triethylamine (2.16 g, 21.3 mmol), and dimethylaminopyridine (49.7 mg, 0.407 mmol) were placed into a two-neck flask equipped with a magnetic stirrer, followed by dilution with 40 ml of dichloromethane. The system was cooled to 0° C., a solution diluted with triphenylchlorosilane (6.0 g, 20.3 mmol) was dropwise added over 1 h. After the dropwise addition, stirring was conducted for 12 h at room temperature, dichloromethane was distilled off and fractionated as a hexane solution, and triphenylbenzyloxysilane, which was a precursor, was obtained at a yield of 89% (6.6 g).

Synthesis Example 7: Synthesis of phenyldimethylbenzyloxysilane (PhMe$_2$Si(OBn))

Benzyl alcohol (3.4 g, 31.4 mmol), triethylamine (3.2 g, 31.6 mmol), and dimethylaminopyridine (36.7 mg, 0.30 mmol) were placed into a two-neck flask equipped with a magnetic stirrer, followed by dilution with 60 ml of dichloromethane. The system was cooled to 00° C., and phenyldimethylchlorosilane (5.1 g, 29.9 mmol) was dropwise added over 3 h. After the dropwise addition, stirring was conducted for 12 h at room temperature, dichloromethane was distilled off and fractionated as a hexane solution, and phenyldimethylbenzyloxysilane, which was a precursor, was obtained at a yield of 90% (6.5 g).

Synthesis Example 8: Synthesis of tetrabenzyloxysilane (Si(OBn)$_4$)

Benzyl alcohol (64.3 g, 594.6 mmol), triethylamine (60.2 g, 594.9 mmol), and dimethylaminopyridine (177.2 mg, 1.45 mmol) were placed into a two-neck flask equipped with a magnetic stirrer, followed by dilution with dichloromethane. The system was cooled to 00° C., and tetrachlorosilane (24.6 g, 145 mmol) was dropwise added over 4 h. After the dropwise addition, stirring was conducted for 12 h at room temperature, dichloromethane was distilled off and fractionated as a hexane solution, and tetrabenzyloxysilane, which was a precursor, was obtained at a yield of 87% (57.7 g).
[Produce of Silanol Compound]
<Investigation of Catalysts>

Example 1

A total of 35.5 mg of ASCA-2 (Pd 4.5 mass %, Pt 0.5 mass %) produced by N.E. Chemcat Corporation (10.0 mol % when calculated based on benzyloxy groups) and triphenylbenzyloxysilane (55.0 mg, 0.150 mmol) obtained in Synthesis Example 6 were placed into a two-neck flask equipped with a magnetic stirrer, and 1.0 ml of tetrahydrofuran (THF) was added thereto. After replacing with hydrogen gas, a reaction was conducted for 1.5 h at room temperature. The catalyst was then filtered out with a filter.
The $^1$H-NMR (THF-d$_8$: 6.1, 7.2-7.4, 7.6-7.7 ppm), $^{13}$C-NMR (THF-d$_8$: 128.2, 128.9, 135.8, 137.9 ppm), $^{29}$Si-NMR (THF-d$_8$: 16.9 ppm) analysis confirmed that triphenylsilanol, etc. was produced. The results relating to the yield of the product, etc. are presented in Table 1.

Comparative Example 1

The reaction was conducted by the same method as in Example 1, except that ASCA-2 was replaced with 16.4 mg of Pd carbon powder PE type (Pd 10 mass %) produced by N.E. Chemcat Corporation. The results relating to the yield of the product, etc. are presented in Table 1.

Comparative Example 2

The reaction was conducted by the same method as in Example 1, except that ASCA-2 was replaced with 32.3 mg of Pd carbon powder NX type (Pd 5 mass %) produced by N.E. Chemcat Corporation. The results relating to the yield of the product, etc. are presented in Table 1.

Comparative Example 3

The reaction was conducted by the same method as in Example 1, except that ASCA-2 was replaced with 16.2 mg of Pd carbon powder OH type (Pd 10 mass %) produced by N.E. Chemcat Corporation. The results relating to the yield of the product, etc. are presented in Table 1.

[C16]

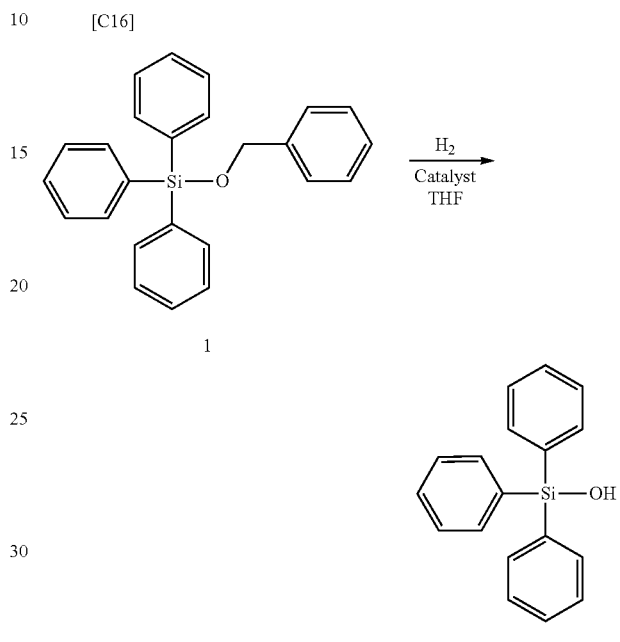

TABLE 1

|  | Conversion ratio [%] | 2 Yield [%] |
| --- | --- | --- |
| Example 1 | 95 | 89 |
| Comparative Example 1 | 14 | 13 |
| Comparative Example 2 | 8 | 6 |
| Comparative Example 3 | 8 | 6 |

<Investigation of Silanol Compound Precursors>

Example 2

A total of 3.9 mg of ASCA-2 (Pd 4.5 mass %, Pt 0.5 mass %) produced by N.E. Chemcat Corporation (1.0 mol % when calculated based on benzyloxy groups) and phenyldimethylbenzyloxysilane (36.3 mg, 0.150 mmol) obtained in Synthesis Example 7 were placed into a two-neck flask equipped with a magnetic stirrer, and 1.0 ml of tetrahydrofuran (THF) was added thereto. After replacing with hydrogen gas, a reaction was conducted for 1.5 h at room temperature. The catalyst was then filtered out with a filter.
The $^1$H-NMR (THF-d$_8$: 0.3, 4.8-5.0, 7.2-7.4, 7.5-7.6 ppm), $^{13}$C-NMR (THF-d$_8$: 0.5, 128.2, 129.6, 133.8, 141.7 ppm), $^{29}$Si-NMR (THF-d$_8$: 1.7 ppm) analysis confirmed that phenyldimethylsilanol was produced. The results relating to the yield of the product, etc. are presented in Table 2.

Example 3

The reaction was conducted by the same method as in Example 2, except that the reaction temperature was changed to 0° C. The results relating to the yield of the product, etc. are presented in Table 2.

Example 4

The reaction was conducted by the same method as in Example 2, except that the reaction temperature was changed to −25° C. The results relating to the yield of the product, etc. are presented in Table 2.

[C17]

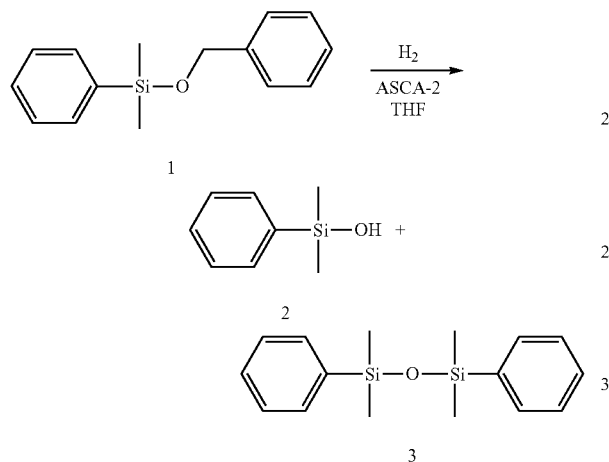

TABLE 2

| | Reaction temperature [° C.] | Conversion ratio [%] | 2 Yield [%] | 3 Yield [%] |
|---|---|---|---|---|
| Example 2 | r.t. | 100 | 51 | 44 |
| Example 3 | 0 | 97 | 63 | 29 |
| Example 4 | −25 | 87 | 66 | 17 |

Example 5

A total of 71.8 mg of ASCA-2 (Pd 4.5 mass %, Pt 0.5 mass %) produced by N.E. Chemcat Corporation (10.0 mol % when calculated based on benzyloxy groups) and diphenyldibenzyloxysilane (61.4 mg, 0.150 mmol) obtained in Synthesis Example 4 were placed into a two-neck flask equipped with a magnetic stirrer, and 1.0 ml of tetrahydrofuran (THF) was added thereto. After replacing with hydrogen gas, a reaction was conducted for 1.5 h at room temperature. The catalyst was then filtered out with a filter. Centrifugal separation was performed, and the reaction solvent was distilled out.

The $^1$H-NMR (THF-$d_8$: 5.5-6.4, 7.2-7.4, 7.6-7.8 ppm), $^{13}$C-NMR (THF-$d_8$: 128.0, 129.9, 135.2, 138.8 ppm), $^{29}$Si-NMR (THF-$d_8$: −33.8 ppm) analysis confirmed that diphenylsilanediol, etc. was produced. The results relating to the yield of the product, etc. are presented in Table 3.

Example 6

The reaction was conducted by the same method as in Example 5, except that the amount of ASCA-2 was changed to 5.0 mol % (35.8 mg) when calculated on the basis of benzyloxy group. The results relating to the yield of the product, etc. are presented in Table 3.

[C18]

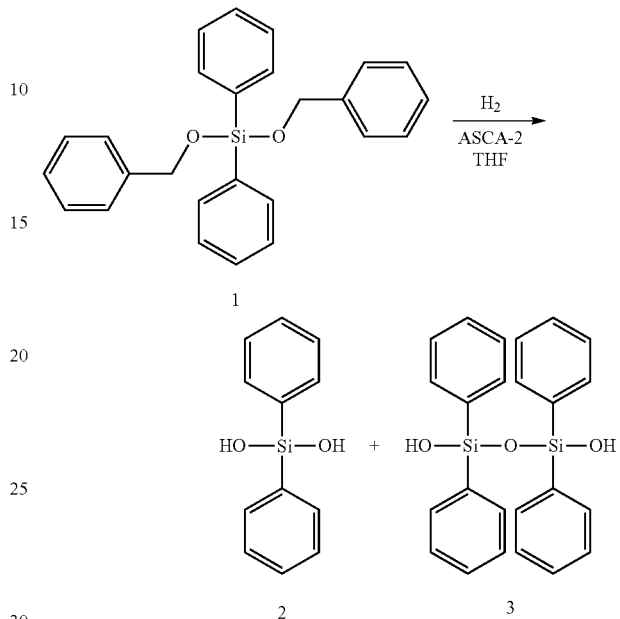

TABLE 3

| | Amount of ASCA-2 used [mol %] | Conversion ratio [%] | 2 Yield [%] | 3 Yield [%] |
|---|---|---|---|---|
| Example 5 | 10 | 100 | 58 | 0 |
| Example 6 | 5 | 98 | 89 | 5 |

Example 7

A total of 10.6 mg of ASCA-2 (Pd 4.5 mass %, Pt 0.5 mass %) produced by N.E. Chemcat Corporation (1.0 mol % when calculated based on benzyloxy groups) and phenyltribenzyloxysilane (63.9 mg, 0.150 mmol) obtained in Synthesis Example 2 were placed into a two-neck flask equipped with a magnetic stirrer, and 1.0 ml of tetrahydrofuran (THF) was added thereto. After replacing with hydrogen gas, a reaction was conducted for 1.5 h at room temperature. The catalyst was then filtered out with a filter.

The $^1$H-NMR (THF-$d_8$: 5.1-6.5, 7.2-7.4, 7.6-7.8 ppm), $^{13}$C-NMR (THF-$d_8$: 127.8, 129.6, 135.1, 138.1 ppm), $^{29}$Si-NMR (THF-$d_8$: −53.3 ppm) analysis confirmed that phenylsilanetriol, etc. was produced. The results relating to the yield of the product, etc. are presented in Table 4.

Example 8

The reaction was conducted by the same method as in Example 7, except that the reaction temperature was changed to −25° C. The results relating to the yield of the product, etc. are presented in Table 4.

Example 9

The reaction was conducted by the same method as in Example 7, except that the amount of ASCA-2 was changed to 3 mol % (32.7 mg) when calculated on the basis of benzyloxy group and the reaction temperature was changed to −25° C. The results relating to the yield of the product, etc. are presented in Table 4.

[C19]

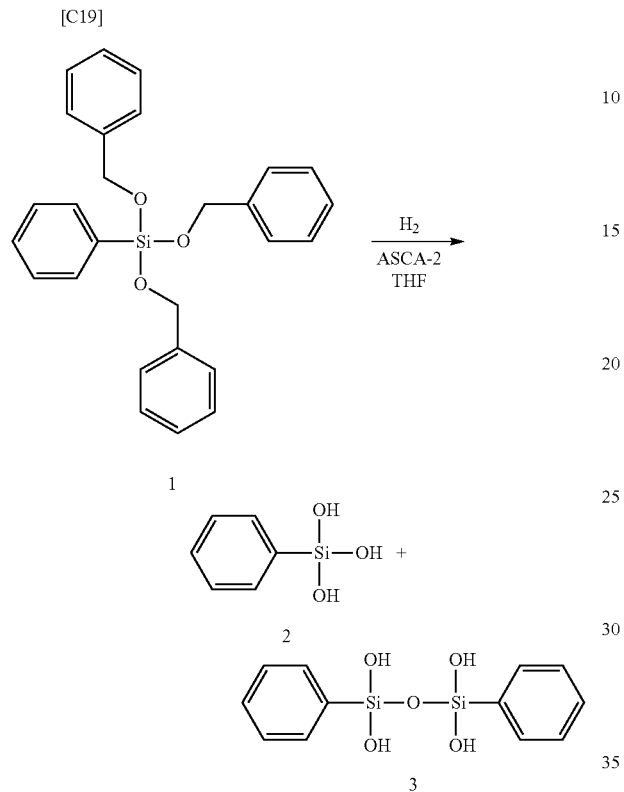

TABLE 4

| | Amount of ASCA-2 used [mol %] | Reaction temperature [° C.] | Conversion ratio [%] | 2 Yield [%] | 3 Yield [%] |
|---|---|---|---|---|---|
| Example 7 | 1 | r.t. | 85 | 22 | 54 |
| Example 8 | 1 | −25 | 37 | 18 | 2 |
| Example 9 | 3 | −25 | 89 | 32 | 40 |

<Investigation of Reaction Solvents>

Example 10

A total of 10.7 mg of ASCA-2 (Pd 4.5 mass %, Pt 0.5 mass %) produced by N.E. Chemcat Corporation (1.0 mol % when calculated based on benzyloxy groups) and phenyltribenzyloxysilane (63.9 mg, 0.150 mmol) obtained in Synthesis Example 2 were placed into a two-neck flask equipped with a magnetic stirrer, and 1.0 ml of N,N-dimethylformamide (DMF) was added thereto. After replacing with hydrogen gas, a reaction was conducted for 6.0 h at room temperature. The catalyst was then filtered out with a filter.

The $^1$H, $^{13}$C, and $^{29}$Si-NMR (DMF/THF-d$_8$: −53.9 ppm) analysis confirmed that phenylsilanetriol, etc. was produced. The results relating to the yield of the product, etc. are presented in Table 5.

Example 11

The reaction was conducted by the same method as in Example 10, except that N,N-dimethylformamide (DMF) was replaced with 1.0 ml of N,N-dimethylacetamide (DMAc). The results relating to the yield of the product, etc. are presented in Table 5.

Example 12

The reaction was conducted by the same method as in Example 10, except that N,N-dimethylformamide (DMF) was replaced with a mixed solution of 0.9 ml of N-methylacetamide (MMAc) and 0.1 ml of N,N-dimethylacetamide (DMAc). The results relating to the yield of the product, etc. are presented in Table 5.

Example 13

The reaction was conducted by the same method as in Example 10, except that N,N-dimethylformamide (DMF) was replaced with a mixed solution of 0.6 ml of acetamide and 0.4 ml of N,N-dimethylacetamide (DMAc). The results relating to the yield of the product, etc. are presented in Table 5.

Example 14

The reaction was conducted by the same method as in Example 10, except that N,N-dimethylformamide (DMF) was replaced with 1.0 ml of dimethylsulfoxide (DMSO). The results relating to the yield of the product, etc. are presented in Table 5.

[C20]

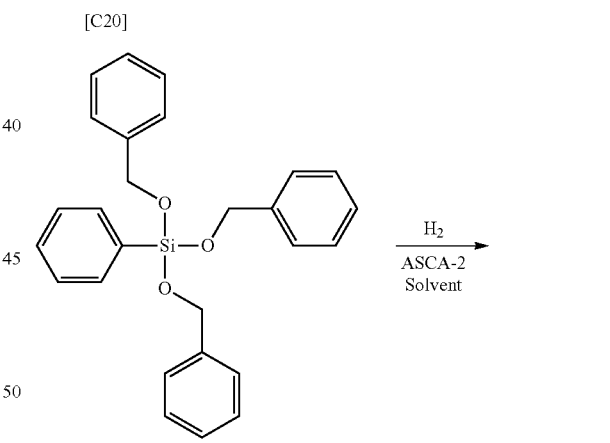

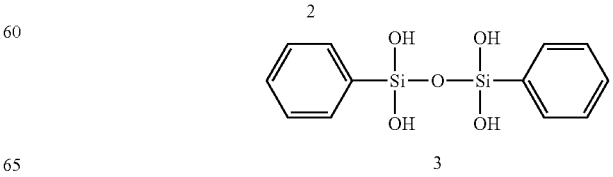

TABLE 5

|  | Reaction solvent | Conversion ratio [%] | 2 Yield [%] | 3 Yield [%] |
|---|---|---|---|---|
| Example 10 | DMF | 100 | 13 | 54 |
| Example 11 | DMAc | 100 | 72 | 17 |
| Example 12 | MMAc + DMAc | 72 | 44 | 0.5 |
| Example 13 | Acetamide + DMAc | 29 | 0.4 | 0 |
| Example 14 | DMSO | 91 | 0 | 12 |

<Investigation of Additives>

Example 15

A total of 32.0 mg of ASCA-2 (Pd 4.5 mass %, Pt 0.5 mass %) produced by N.E. Chemcat Corporation (3.0 mol % when calculated based on benzyloxy groups) and phenyltribenzyloxysilane (63.9 mg, 0.150 mmol) obtained in Synthesis Example 2 were placed into a two-neck flask equipped with a magnetic stirrer, and 1.0 ml of N,N-dimethylacetamide (DMAc) and aniline ($NH_2Ph$, 1.3 mg) in a 0.030-fold substance amount, when calculated based on benzyloxy groups, were added thereto. After replacing with hydrogen gas, a reaction was conducted for 6.0 h at room temperature. The catalyst was then filtered out with a filter.

The $^1H$, $^{13}C$-NMR (DMAc/THF-$d_8$: 127.9, 129.2, 135.3, 139.3 ppm), and $^{29}Si$-NMR (DMAc/THF-$d_8$: −54.9 ppm) analysis confirmed that phenylsilanetriol, etc. was produced. The results relating to the yield of the product, etc. are presented in Table 6.

Example 16

The reaction was conducted by the same method as in Example 15, except that aniline ($NH_2Ph$) was replaced with diphenylamine ($NHPh_2$, 2.3 mg) in a 0.030-fold substance amount, when calculated based on benzyloxy groups. The results relating to the yield of the product, etc. are presented in Table 6.

Example 17

The reaction was conducted by the same method as in Example 15, except that aniline ($NH_2Ph$) was replaced with diphenylamine ($NHPh_2$, 4.6 mg) in a 0.060-fold substance amount, when calculated based on benzyloxy groups. The results relating to the yield of the product, etc. are presented in Table 6.

Example 18

The reaction was conducted by the same method as in Example 15, except that aniline ($NH_2Ph$) was replaced with diphenylamine ($NHPh_2$, 5.7 mg) in a 0.075-fold substance amount, when calculated based on benzyloxy groups. The results relating to the yield of the product, etc. are presented in Table 6.

Example 19

The reaction was conducted by the same method as in Example 15, except that aniline ($NH_2Ph$) was replaced with dimethylpyridine ($Me_2Pyr$, 1.5 mg) in a 0.030-fold substance amount, when calculated based on benzyloxy groups. The results relating to the yield of the product, etc. are presented in Table 6.

Example 20

The reaction was conducted by the same method as in Example 15, except that aniline ($NH_2Ph$) was replaced with di-tert-butylpyridine ($^tBu_2Pyr$, 2.7 mg) in a 0.030-fold substance amount, when calculated based on benzyloxy groups. The results relating to the yield of the product, etc. are presented in Table 6.

Example 21

The reaction was conducted by the same method as in Example 15, except that aniline ($NH_2Ph$) was replaced with pyrazine (Pyraz, 1.1 mg) in a 0.030-fold substance amount, when calculated based on benzyloxy groups. The results relating to the yield of the product, etc. are presented in Table 6.

Example 22

The reaction was conducted by the same method as in Example 15, except that aniline ($NH_2Ph$) was replaced with triphenylamine ($NPh_3$, 3.4 mg) in a 0.030-fold substance amount, when calculated based on benzyloxy groups. The results relating to the yield of the product, etc. are presented in Table 6.

[C21]

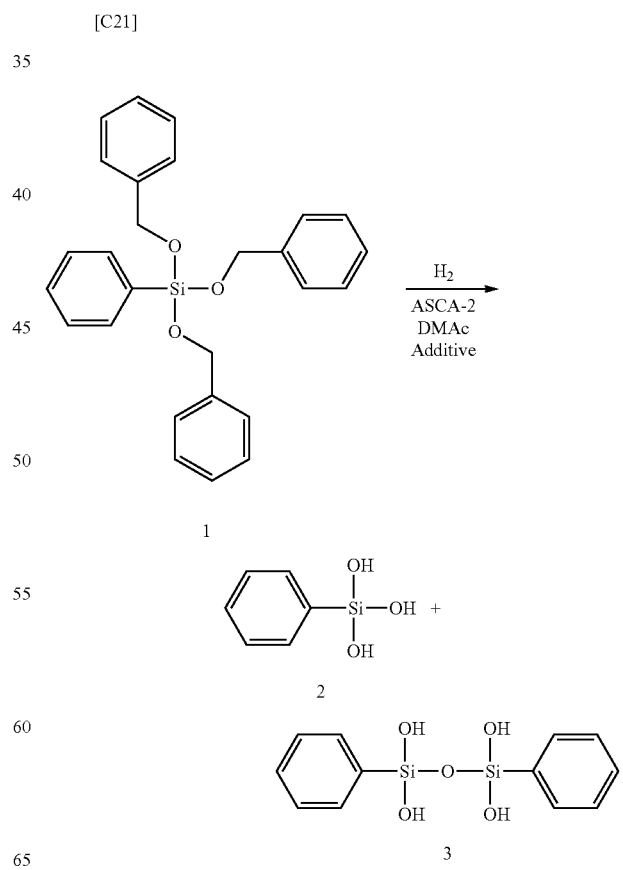

TABLE 6

| | Additive | | Conversion ratio [%] | 2 Yield [%] | 3 Yield [%] |
|---|---|---|---|---|---|
| | Type | Amount added [amine/benzyloxy groups] | | | |
| Example 15 | NH₂Ph | 0.030 | 100 | 85 | 6 |
| Example 16 | NHPh₂ | 0.030 | 100 | 78 | 20 |
| Example 17 | | 0.060 | 100 | 84 | 13 |
| Example 18 | | 0.075 | 100 | 85 | 10 |
| Example 19 | Me₂Pyr | 0.030 | 100 | 72 | 24 |
| Example 20 | tBu₂Pyr | 0.030 | 100 | 58 | 34 |
| Example 21 | Pyraz | 0.030 | 84 | 0 | 0 |
| Example 22 | NPh₃ | 0.030 | 100 | 67 | 31 |

Example 23

A total of 21.3 mg of ASCA-2 (Pd 4.5 mass %, Pt 0.5 mass %) produced by N.E. Chemcat Corporation (2.0 mol % when calculated based on benzyloxy groups) and phenyltribenzyloxysilane (63.9 mg, 0.150 mmol) obtained in Synthesis Example 2 were placed into a two-neck flask equipped with a magnetic stirrer, and 1.0 ml of N,N-dimethylacetamide (DMAc) and diphenylamine (NHPh₂, 25.4 mg) in a 0.333-fold substance amount, when calculated based on benzyloxy groups, were added thereto. After replacing with hydrogen gas, a reaction was conducted for 6 h at room temperature. The catalyst was then filtered out with a filter.

The $^1$H, $^{13}$C-NMR (DMAc/THF-d₈: 127.9, 129.2, 135.3, 139.3 ppm), and $^{29}$Si-NMR (DMAc/THF-d₈: −54.9 ppm) analysis confirmed that phenylsilanetriol, etc. was produced. The results relating to the yield of the product, etc. are presented in Table 7.

Example 24

The reaction was conducted by the same method as in Example 23, except that the amount of ASCA-2 was changed to 4.0 mol % (42.8 mg) when calculated based on benzyloxy groups. The results relating to the yield of the product, etc. are presented in Table 7.

Example 25

The reaction was conducted by the same method as in Example 23, except that the amount of ASCA-2 was changed to 6.0 mol % (64.3 mg) when calculated based on benzyloxy groups. The results relating to the yield of the product, etc. are presented in Table 7.

[C22]

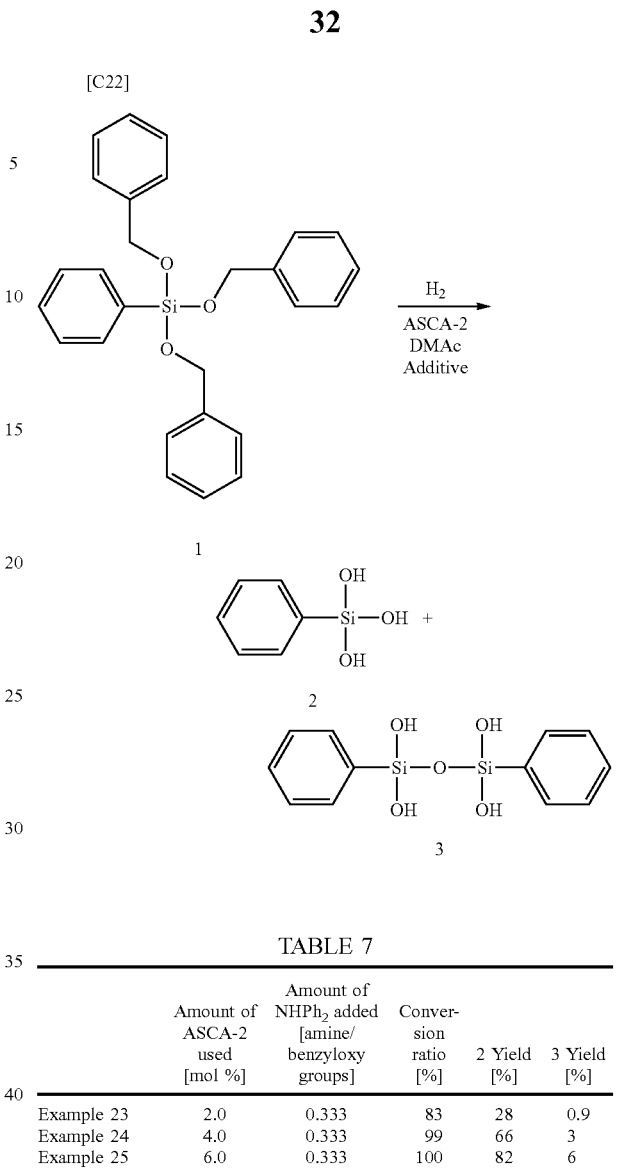

TABLE 7

| | Amount of ASCA-2 used [mol %] | Amount of NHPh₂ added [amine/benzyloxy groups] | Conversion ratio [%] | 2 Yield [%] | 3 Yield [%] |
|---|---|---|---|---|---|
| Example 23 | 2.0 | 0.333 | 83 | 28 | 0.9 |
| Example 24 | 4.0 | 0.333 | 99 | 66 | 3 |
| Example 25 | 6.0 | 0.333 | 100 | 82 | 6 |

Example 26

A total of 28.5 mg of ASCA-2 (Pd 4.5 mass %, Pt 0.5 mass %) produced by N.E. Chemcat Corporation (2.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of N,N-dimethylacetamide (DMAc) and aniline (NH₂Ph, 1.1 mg) in a 0.020-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C, and $^{29}$Si-NMR (DMAc/THF-d₈: −72.1 ppm) analysis confirmed that silanetetraol, etc. was produced. The results relating to the yield of the product, etc. are presented in Table 8.

Example 27

The reaction was conducted by the same method as in Example 26, except that the amount of aniline (NH₂Ph) was changed to a 0.030-fold substance amount, when calculated based on benzyloxy groups. The results relating to the yield of the product, etc. are presented in Table 8.

Example 28

The reaction was conducted by the same method as in Example 26, except that the amount of aniline (NH$_2$Ph) was changed to a 0.040-fold substance amount, when calculated based on benzyloxy groups. The results relating to the yield of the product, etc. are presented in Table 8.

[C23]

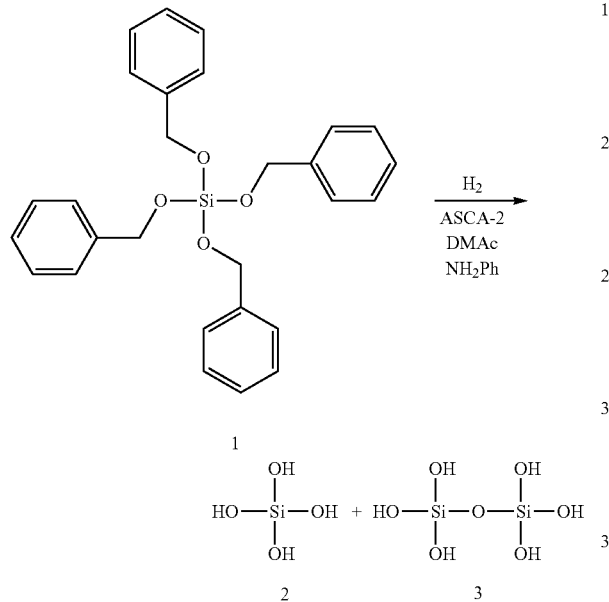

TABLE 8

| | Amount of NH$_2$Ph added [amine/benzyloxy groups] | Conversion ratio [%] | 2 Yield [%] | 3 Yield [%] |
|---|---|---|---|---|
| Example 26 | 0.020 | 100 | 57 | 26 |
| Example 27 | 0.030 | 100 | 76 | 8 |
| Example 28 | 0.040 | 100 | 45 | 3 |

<Investigation of Reaction Time>

Example 29

A total of 10.8 mg of ASCA-2 (Pd 4.5 mass %, Pt 0.5 mass %) produced by N.E. Chemcat Corporation (1.0 mol % when calculated based on benzyloxy groups) and phenyltribenzyloxysilane (63.9 mg, 0.150 mmol) obtained in Synthesis Example 2 were placed into a two-neck flask equipped with a magnetic stirrer, and 1.0 ml of N,N-dimethylacetamide (DMAc) was added thereto. After replacing with hydrogen gas, a reaction was conducted for 1.5 h at room temperature. The catalyst was then filtered out with a filter.

The $^1$H, $^{13}$C-NMR (DMAc/THF-d$_8$: 127.9, 129.2, 135.3, 139.3 ppm), and $^{29}$Si-NMR (DMAc/THF-d$_8$: −54.9 ppm) analysis confirmed that phenylsilanetriol, etc. was produced. The results relating to the yield of the product, etc. are presented in Table 9.

Example 30

The reaction was conducted by the same method as in Example 29, except that the reaction time was changed to 3.0 h. The results relating to the yield of the product, etc. are presented in Table 9.

Example 31

The reaction was conducted by the same method as in Example 29, except that the reaction time was changed to 6.0 h. The results relating to the yield of the product, etc. are presented in Table 9.

[C24]

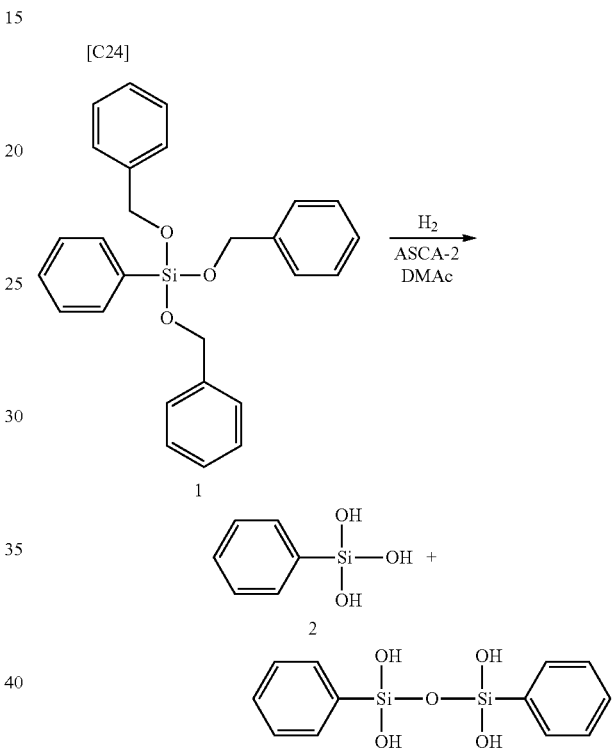

TABLE 9

| | Reaction time [h] | Conversion ratio [%] | 2 Yield [%] | 3 Yield [%] |
|---|---|---|---|---|
| Example 29 | 1.5 | 55 | 13 | 0 |
| Example 30 | 3.0 | 82 | 36 | 5 |
| Example 31 | 6.0 | 100 | 72 | 17 |

Example 32

A total of 28.5 mg of ASCA-2 (Pd 4.5 mass %, Pt 0.5 mass %) produced by N.E. Chemcat Corporation (2.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of N,N-dimethylacetamide (DMAc) was added thereto. After replacing with hydrogen gas, a reaction was conducted for 1.0 h at room temperature. The catalyst was then filtered out with a filter.

The $^1$H, $^{13}$C, and $^{29}$Si-NMR (DMAc/THF-d$_8$: −72.1 ppm) analysis confirmed that silanetetraol, etc. was produced. The results relating to the yield of the product are presented in Table 10.

Example 33

The reaction was conducted by the same method as in Example 32, except that the reaction time was changed to 2.0 h. The results relating to the yield of the product, etc. are presented in Table 10.

[C25]

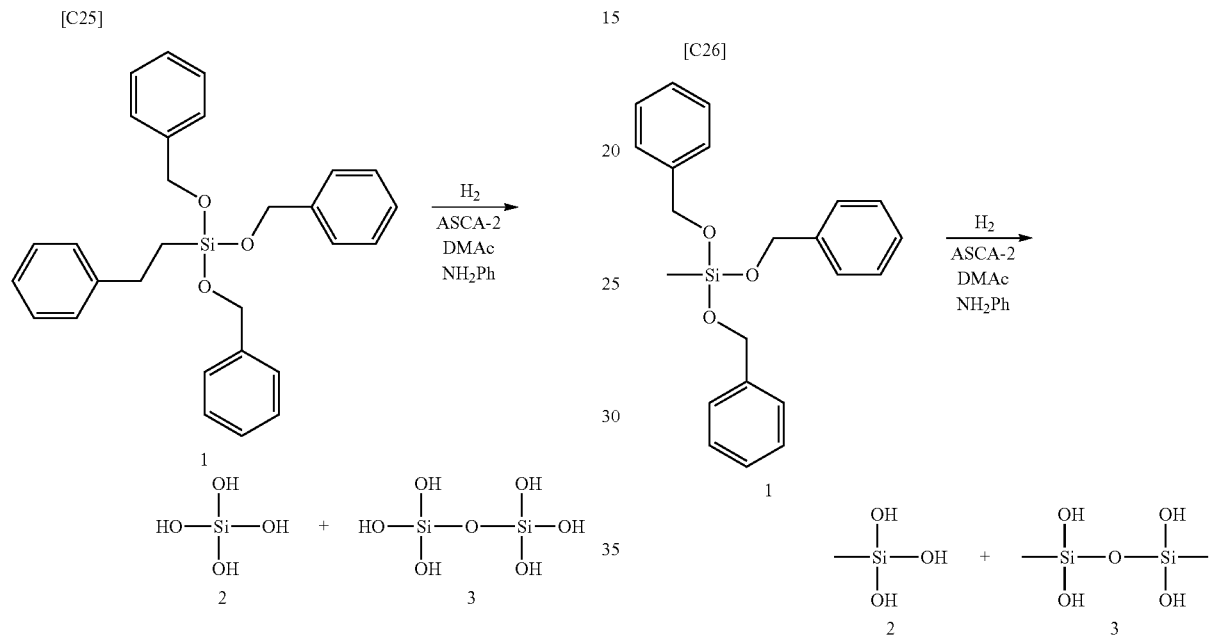

TABLE 10

|  | Reaction time [h] | Conversion ratio [%] | 2 Yield [%] | 3 Yield [%] |
| --- | --- | --- | --- | --- |
| Example 32 | 1.0 | 100 | 37 | 14 |
| Example 33 | 2.0 | 100 | 57 | 26 |

Example 34

A total of 10.7 mg of ASCA-2 (Pd 4.5 mass %, Pt 0.5 mass %) produced by N.E. Chemcat Corporation (1.0 mol % when calculated based on benzyloxy groups) and methyltribenzyloxysilane (54.7 mg, 0.150 mmol) obtained in Synthesis Example 1 were placed into a two-neck flask equipped with a magnetic stirrer, and 0.8 ml of N,N-dimethylacetamide (DMAc) and aniline (NH$_2$Ph, 0.8 mg) in a 0.019-fold substance amount, when calculated based on benzyloxy groups, were added thereto. After replacing with hydrogen gas, a reaction was conducted for 1.0 h at room temperature. The catalyst was then filtered out with a filter.

The $^1$H, $^{13}$C-NMR (DMAc/THF-d$_8$: −2.2 ppm), and $^{29}$Si-NMR (DMAc/THF-d$_8$: −41.5 ppm) analysis confirmed that methylsilanetriol, etc. was produced. The results relating to the yield of the product are presented in Table 11.

Example 35

The reaction was conducted by the same method as in Example 34, except that the reaction time was changed to 2.0 h. The results relating to the yield of the product, etc. are presented in Table 11.

Example 36

The reaction was conducted by the same method as in Example 34, except that the reaction time was changed to 3.0 h. The results relating to the yield of the product, etc. are presented in Table 11.

[C26]

TABLE 11

|  | Reaction time [h] | Conversion ratio [%] | 2 Yield [%] | 3 Yield [%] |
| --- | --- | --- | --- | --- |
| Example 34 | 1.0 | 91 | 22 | 4 |
| Example 35 | 2.0 | 100 | 60 | 8 |
| Example 36 | 3.0 | 100 | 55 | 8 |

<Other Factors (Various Conditions)>

Example 37

A total of 9.1 mg of ASCA-2 (Pd 4.5 mass %, Pt 0.5 mass %) produced by N.E. Chemcat Corporation (2.5 mol % when calculated based on benzyloxy groups) and trimethylbenzyloxysilane (27.0 mg, 0.150 mmol) obtained in Synthesis Example 5 were placed into a two-neck flask equipped with a magnetic stirrer, and 1.6 ml of N,N-dimethylacetamide (DMAc) and aniline (NH$_2$Ph, 0.9 mg) in a 0.064-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C-NMR (DMAc/THF-d$_8$: 2.1 ppm), and $^{29}$Si-NMR (DMAc/THF-d$_8$: 10.1 ppm) analysis confirmed that trimethylsilanol, etc. was produced. The results relating to the yield of the product, etc. are presented in Table 12.

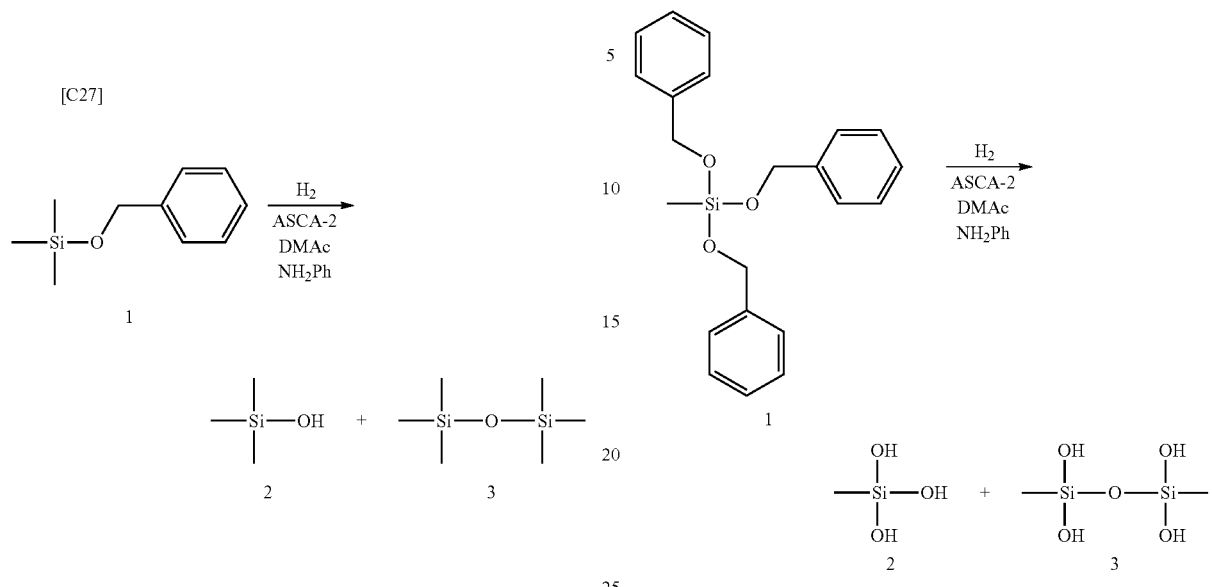

[C27]

TABLE 12

|  | Conversion ratio [%] | 2 Yield [%] | 3 Yield [%] |
| --- | --- | --- | --- |
| Example 37 | 100 | 97 | 2 |

Example 38

A total of 10.8 mg of ASCA-2 (Pd 4.5 mass %, Pt 0.5 mass %) produced by N.E. Chemcat Corporation (1.0 mol % when calculated based on benzyloxy groups) and methyltribenzyloxysilane (54.7 mg, 0.150 mmol) obtained in Synthesis Example 1 were placed into a two-neck flask equipped with a magnetic stirrer, and 0.8 ml of N,N-dimethylacetamide (DMAc) and aniline ($NH_2Ph$, 0.8 mg) in a 0.019-fold substance amount, when calculated based on benzyloxy groups, were added thereto. After replacing with hydrogen gas, a reaction was conducted for 2.0 h at room temperature. The catalyst was then filtered out with a filter.

The $^1H$, $^{13}C$-NMR (DMAc/THF-$d_8$: −2.2 ppm), and $^{29}Si$-NMR (DMAc/THF-$d_8$: −41.5 ppm) analysis confirmed that methylsilanetriol was produced. The results relating to the yield of the product, etc. are presented in Table 13.

Example 39

The reaction was conducted by the same method as in Example 38, except that the amount of ASCA-2 was changed to 2.0 mol % (21.8 mg), when calculated on the basis of benzyloxy groups, the amount of dimethylacetamide (DMAc) was changed to 1.6 ml, and the amount of aniline ($NH_2Ph$) was changed to a 0.038-fold substance amount, when calculated based on benzyloxy groups. The results relating to the yield of the product, etc. are presented in Table 13.

[C28]

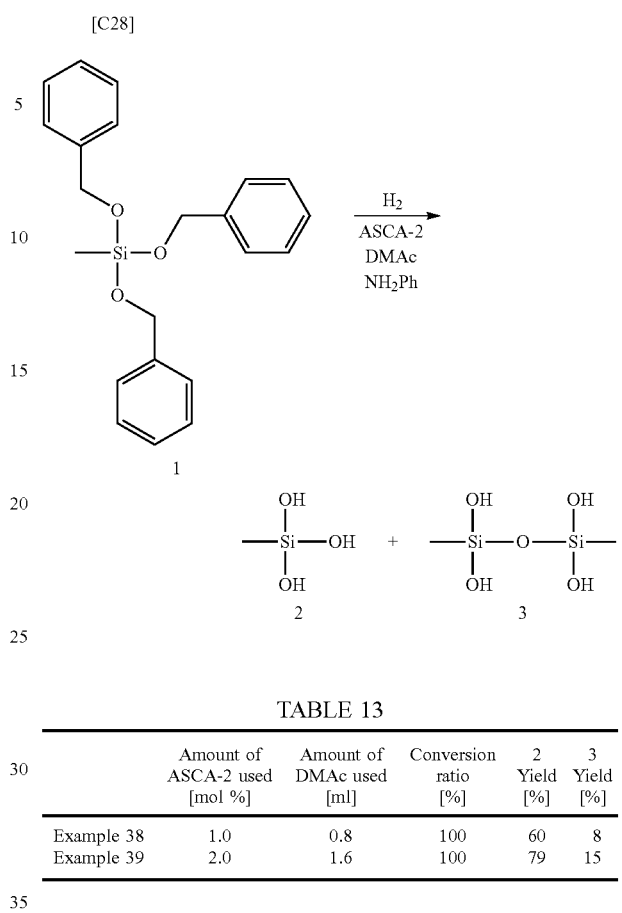

TABLE 13

|  | Amount of ASCA-2 used [mol %] | Amount of DMAc used [ml] | Conversion ratio [%] | 2 Yield [%] | 3 Yield [%] |
| --- | --- | --- | --- | --- | --- |
| Example 38 | 1.0 | 0.8 | 100 | 60 | 8 |
| Example 39 | 2.0 | 1.6 | 100 | 79 | 15 |

Example 40

A total of 21.4 mg of ASCA-2 (Pd 4.5 mass %, Pt 0.5 mass %) produced by N.E. Chemcat Corporation (2.0 mol % when calculated based on benzyloxy groups) and methyltribenzyloxysilane (54.7 mg, 0.150 mmol) obtained in Synthesis Example 1 were placed into a two-neck flask equipped with a magnetic stirrer, and 1.6 ml of N,N-dimethylacetamide (DMAc) and aniline ($NH_2Ph$, 2.1 mg) in a 0.050-fold substance amount, when calculated based on benzyloxy groups, were added thereto. After replacing with hydrogen gas, a reaction was conducted for 2.0 h at room temperature. The catalyst was then filtered out with a filter.

The $^1H$, $^{13}C$-NMR (DMAc/THF-$d_8$: −2.2 ppm), and $^{29}Si$-NMR (DMAc/THF-$d_8$: −41.5 ppm) analysis confirmed that methylsilanetriol, etc. was produced. The results relating to the yield of the product, etc. are presented in Table 14.

Example 41

The reaction was conducted by the same method as in Example 40, except that the amount of ASCA-2 was changed to 2.5 mol % (26.7 mg), when calculated on the basis of benzyloxy groups, and the amount of aniline ($NH_2Ph$) was changed to a 0.063-fold substance amount, when calculated based on benzyloxy groups. The results relating to the yield of the product, etc. are presented in Table 14.

[C29]

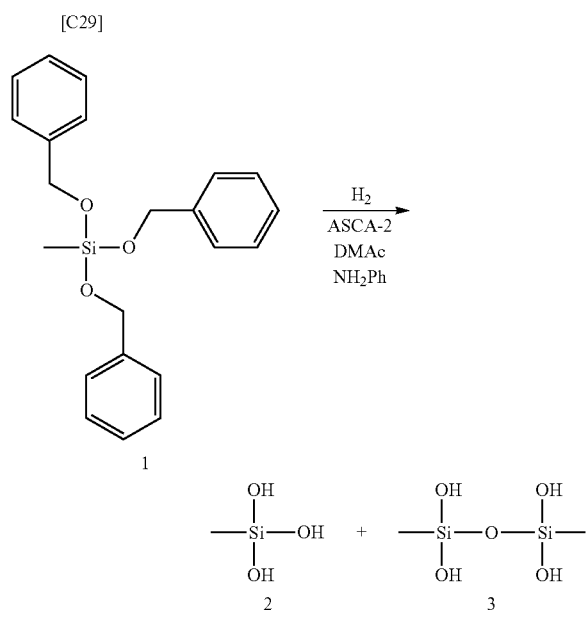

TABLE 14

|  | Amount of ASCA-2 used [mol %] | Amount of NH$_2$Ph used [amine/ benzyloxy groups] | Conversion ratio [%] | 2 Yield [%] | 3 Yield [%] |
|---|---|---|---|---|---|
| Example 40 | 2.0 | 0.050 | 100 | 75 | 8 |
| Example 41 | 2.5 | 0.063 | 100 | 80 | 8 |

Example 42

A total of 17.9 mg of ASCA-2 (Pd 4.5 mass %, Pt 0.5 mass %) produced by N.E. Chemcat Corporation (2.5 mol % when calculated based on benzyloxy groups) and dimethyldibenzyloxysilane (40.8 mg, 0.150 mmol) obtained in Synthesis Example 3 were placed into a two-neck flask equipped with a magnetic stirrer, and 1.6 ml of N,N-dimethylacetamide (DMAc) and aniline (NH$_2$Ph, 1.8 mg) in a 0.063-fold substance amount, when calculated based on benzyloxy groups, were added thereto. After replacing with hydrogen gas, a reaction was conducted for 2.0 h at room temperature. The catalyst was then filtered out with a filter. The $^1$H, $^{13}$C-NMR (DMAc/THF-d$_8$: 0.7 ppm), and $^{29}$Si-NMR (DMAc/THF-d$_8$: −9.6 ppm) analysis confirmed that dimethylsilanediol, etc. was produced. The results relating to the yield of the product, etc. are presented in Table 15.

Example 43

The reaction was conducted by the same method as in Example 42, except that the amount of aniline (NH$_2$Ph) was changed to a 0.075-fold substance amount, when calculated based on benzyloxy groups. The results relating to the yield of the product, etc. are presented in Table 15.

Example 44

The reaction was conducted by the same method as in Example 42, except that the amount of aniline (NH$_2$Ph) was changed to a 0.088-fold substance amount, when calculated based on benzyloxy groups. The results relating to the yield of the product, etc. are presented in Table 15.

Example 45

The reaction was conducted by the same method as in Example 42, except that the amount of aniline (NH$_2$Ph) was changed to a 0.100-fold substance amount, when calculated based on benzyloxy groups. The results relating to the yield of the product, etc. are presented in Table 15.

Example 46

The reaction was conducted by the same method as in Example 42, except that the amount of ASCA-2 was changed to 3.0 mol % (21.5 mg), when calculated on the basis of benzyloxy groups, and the amount of aniline (NH$_2$Ph) was changed to a 0.106-fold substance amount, when calculated based on benzyloxy groups. The results relating to the yield of the product, etc. are presented in Table 15.

Example 47

The reaction was conducted by the same method as in Example 42, except that the amount of ASCA-2 was changed to 3.5 mol % (25.2 mg), when calculated on the basis of benzyloxy groups, and the amount of aniline (NH$_2$Ph) was changed to a 0.123-fold substance amount, when calculated based on benzyloxy groups. The results relating to the yield of the product, etc. are presented in Table 15.

[C30]

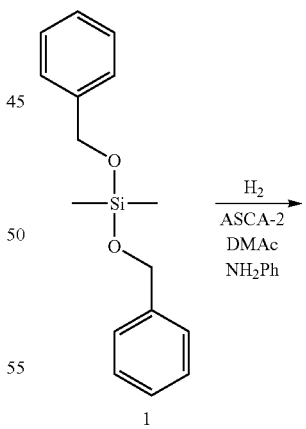

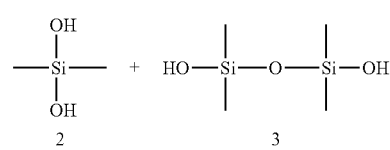

TABLE 15

|  | Amount of ASCA-2 used [mol %] | Amount of NH₂Ph used [amine/benzyloxy groups] | Conversion ratio [%] | 2 Yield [%] | 3 Yield [%] |
|---|---|---|---|---|---|
| Example 42 | 2.5 | 0.063 | 100 | 84 | 13 |
| Example 43 | 2.5 | 0.075 | 100 | 85 | 10 |
| Example 44 | 2.5 | 0.088 | 100 | 87 | 6 |
| Example 45 | 2.5 | 0.100 | 100 | 80 | 6 |
| Example 46 | 3.0 | 0.106 | 100 | 88 | 6 |
| Example 47 | 3.5 | 0.123 | 100 | 88 | 6 |

Example 48

A total of 28.7 mg of ASCA-2 (Pd 4.5 mass %, Pt 0.5 mass %) produced by N.E. Chemcat Corporation (2.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of N,N-dimethylacetamide (DMAc) and aniline (NH₂Ph, 2.2 mg) in a 0.039-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C, and $^{29}$Si-NMR (DMAc/THF-d₈: −72.1 ppm) analysis confirmed that silanetetraol, etc. was produced. The results relating to the yield of the product are presented in Table 16.

Example 49

The reaction was conducted by the same method as in Example 48, except that the amount of ASCA-2 was changed to 2.5 mol % (36.0 mg), when calculated on the basis of benzyloxy groups, and the amount of aniline (NH₂Ph) was changed to a 0.049-fold substance amount, when calculated based on benzyloxy groups. The results relating to the yield of the product, etc. are presented in Table 16.

Example 50

The reaction was conducted by the same method as in Example 48, except that the amount of ASCA-2 was changed to 3.0 mol % (43.2 mg), when calculated on the basis of benzyloxy groups, and the amount of aniline (NH₂Ph) was changed to a 0.059-fold substance amount, when calculated based on benzyloxy groups. The results relating to the yield of the product, etc. are presented in Table 16.

Example 51

The reaction was conducted by the same method as in Example 48, except that the amount of ASCA-2 was changed to 3.5 mol % (50.0 mg), when calculated on the basis of benzyloxy groups, and the amount of aniline (NH₂Ph) was changed to a 0.068-fold substance amount, when calculated based on benzyloxy groups. The results relating to the yield of the product, etc. are presented in Table 16.

[C31]

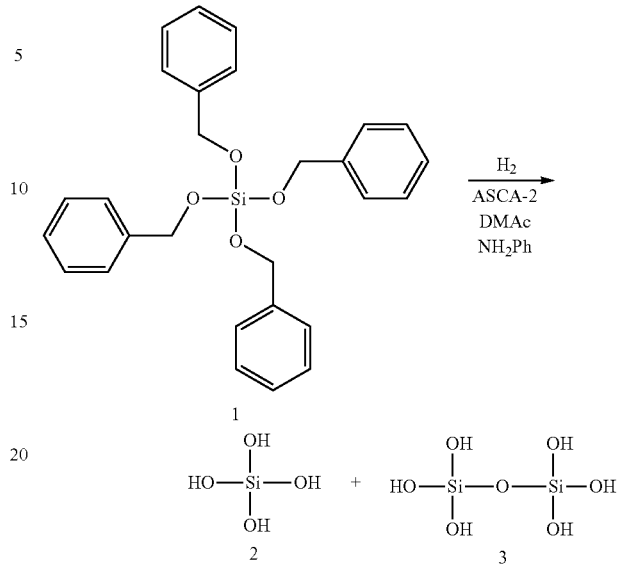

TABLE 16

|  | Amount of ASCA-2 used [mol %] | Conversion ratio [%] | 2 Yield [%] | 3 Yield [%] |
|---|---|---|---|---|
| Example 48 | 2.0 | 100 | 45 | 3 |
| Example 49 | 2.5 | 100 | 66 | 4 |
| Example 50 | 3.0 | 100 | 78 | 5 |
| Example 51 | 3.5 | 100 | 90 | 8 |

Example 52

A total of 28.4 mg of ASCA-2 (Pd 4.5 mass %, Pt 0.5 mass %) produced by N.E. Chemcat Corporation (2.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of N,N-dimethylacetamide (DMAc) was added thereto. After replacing with hydrogen gas, a reaction was conducted for 2.0 h at room temperature. The catalyst was then filtered out with a filter.

The $^1$H, $^{13}$C, and $^{29}$Si-NMR (DMAc/THF-d₈: −72.1 ppm) analysis confirmed that silanetetraol, etc. was produced. The results relating to the yield of the product, etc. are presented in Table 17.

Example 53

The reaction was conducted by the same method as in Example 52, except that N,N-dimethylacetamide (DMAc) was replaced with a mixed solution of 1.4 ml of N-methylacetamide (MMAc) and 0.2 ml of N,N-dimethylacetamide (DMAc). The results relating to the yield of the product, etc. are presented in Table 17.

Example 54

The reaction was conducted by the same method as in Example 52, except that N,N-dimethylacetamide (DMAc) was replaced with a mixed solution of 0.4 ml of acetamide and 1.2 ml of N,N-dimethylacetamide (DMAc). The results relating to the yield of the product, etc. are presented in Table 17.

[C32]

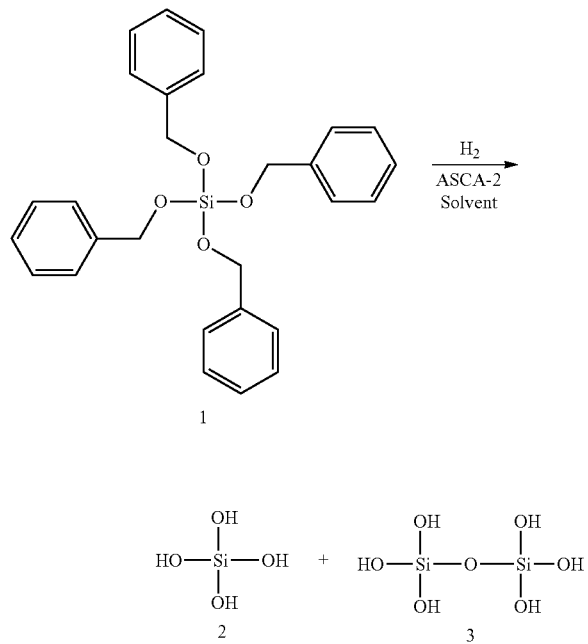

TABLE 17

|  | Reaction solvent | Conversion ratio [%] | 2 Yield [%] | 3 Yield [%] |
| --- | --- | --- | --- | --- |
| Example 52 | DMAc | 100 | 13 | 34 |
| Example 53 | MMAc + DMAc | 100 | 85 | 13 |
| Example 54 | Acetamide + DMAc | 100 | 42 | 38 |

Example 55

A total of 43.0 mg of ASCA-2 (Pd 4.5 mass %, Pt 0.5 mass %) produced by N.E. Chemcat Corporation (3.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.4 ml of N-methylacetamide (MMAc), 0.2 ml of N,N-dimethylacetamide (DMAc), and aniline ($NH_2Ph$, 1.7 mg) in a 0.030-fold substance amount, when calculated based on benzyloxy groups, were added thereto. After replacing with hydrogen gas, a reaction was conducted for 2.0 h at room temperature. The catalyst was then filtered out with a filter.

The $^1H$, $^{13}C$, and $^{29}Si$-NMR (DMAc/THF-$d_8$: −72.4 ppm) analysis confirmed that silanetetraol, etc. was produced. The results relating to the yield of the product, etc. are presented in Table 18.

[C33]

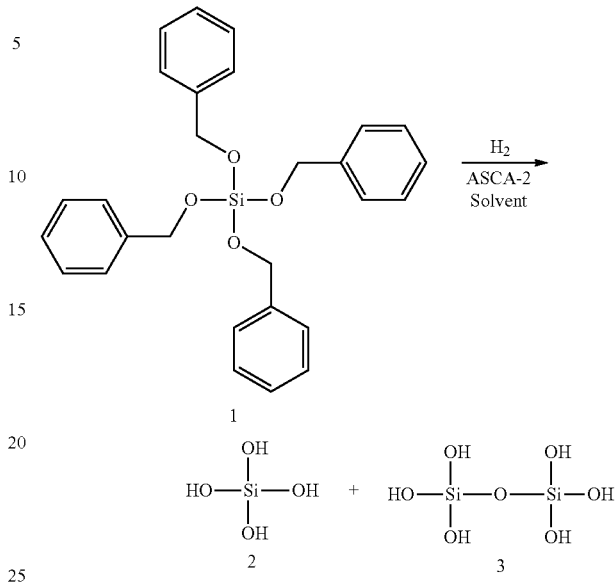

TABLE 18

|  | Reaction solvent | Amount of $NH_2Ph$ used [amine/benzyloxy groups] | Conversion ratio [%] | 2 Yield [%] | 3 Yield [%] |
| --- | --- | --- | --- | --- | --- |
| Example 55 | MMAc + DMAc | 0.030 | 100 | 96 | 4 |

Example 56

A total of 28.8 mg of ASCA-2 (Pd 4.5 mass %, Pt 0.5 mass %) produced by N.E. Chemcat Corporation (2.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of tetramethylurea ($Me_4Urea$) was added thereto. After replacing with hydrogen gas, a reaction was conducted for 2.0 h at room temperature. The catalyst was then filtered out with a filter.

The $^1H$, $^{13}C$, and $^{29}Si$-NMR ($Me_4Urea$/THF-$d_8$: −83.0 ppm) analysis and time-of-flight mass spectrometry (TOFMS)(m/z: [MCl]$^-$, $ClH_6O_9Si_3$, calculated value 268.9014, actually measured value: 268.9025) confirmed that cyclic trisiloxanehexaol, etc. was produced. The results relating to the yield of the product, etc. are presented in Table 19.

Example 57

The reaction was conducted by the same method as in Example 56, except that tetramethylurea ($Me_4Urea$) was replaced with of N,N-dimethylacetamide (DMAc). The results relating to the yield of the product, etc. are presented in Table 19.

[C34]

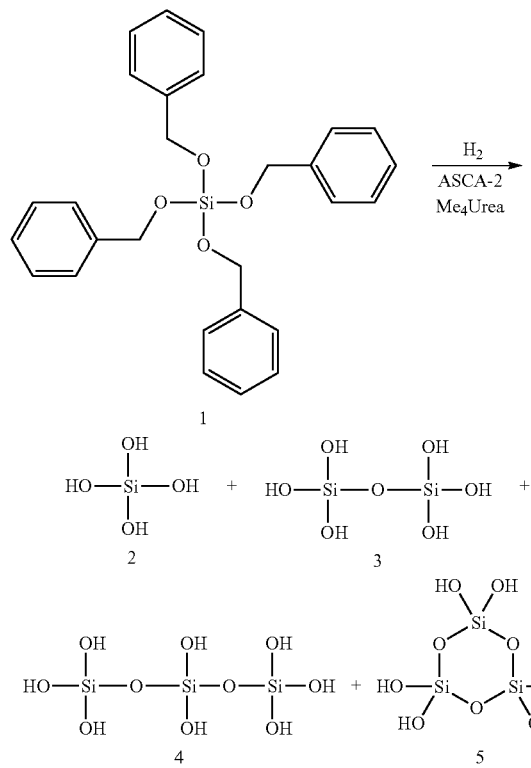

TABLE 19

|  | Amount of ASCA-2 used [mol %] | Conversion ratio [%] | 2 Yield [%] | 3 Yield [%] | 4 Yield [%] | 5 Yield [%] |
|---|---|---|---|---|---|---|
| Example 56 | 2.0 | 100 | 8 | 36 | 0 | 47 |
| Example 57 | 2.0 | 100 | 13 | 34 | 0 | 39 |

Example 58

A total of 50.2 mg of ASCA-2 (Pd 4.5 mass %, Pt 0.5 mass %) produced by N.E. Chemcat Corporation (3.5 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of tetramethylurea (Me$_4$Urea) and aniline (NH$_2$Ph, 2.0 mg) in a 0.035-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C, and $^{29}$Si-NMR (Me$_4$Urea/THF-d$_8$: −71.7 ppm) analysis confirmed that silanetetraol, etc. was produced. The results relating to the yield of the product, etc. are presented in Table 20.

Example 59

The reaction was conducted by the same method as in Example 58, except that the amount of aniline (NH$_2$Ph) was changed to a 0.044-fold substance amount, when calculated based on benzyloxy groups. The results relating to the yield of the product, etc. are presented in Table 20.

Example 60

The reaction was conducted by the same method as in Example 58, except that the amount of aniline (NH$_2$Ph) was changed to a 0.070-fold substance amount, when calculated based on benzyloxy groups. The results relating to the yield of the product, etc. are presented in Table 20.

[C35]

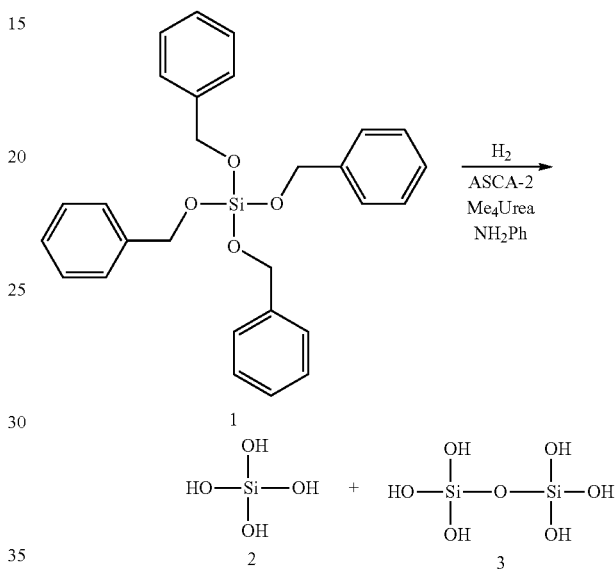

TABLE 20

|  | Amount of ASCA-2 used [mol %] | Amount of NH$_2$Ph used [amine/benzyloxy groups] | Conversion ratio [%] | 2 Yield [%] | 3 Yield [%] |
|---|---|---|---|---|---|
| Example 58 | 3.5 | 0.035 | 100 | 77 | 20 |
| Example 59 | 3.5 | 0.044 | 100 | 92 | 6 |
| Example 60 | 3.5 | 0.070 | 100 | 19 | 0 |

Example 61

A total of 99.2 mg of ASCA-2 (Pd 4.5 mass %, Pt 0.5 mass %) produced by N.E. Chemcat Corporation (3.5 mol % when calculated based on benzyloxy groups) and tetrabenzyloxysilane (137.0 mg, 0.300 mmol) obtained in Synthesis Example 8 were placed into a two-neck flask equipped with a magnetic stirrer, and 1.6 ml of tetramethylurea (Me$_4$Urea) and aniline (NH$_2$Ph, 4.9 mg) in a 0.044-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C, and $^{29}$Si-NMR (Me$_4$Urea/THF-d$_8$: −71.7 ppm) analysis confirmed that silanetetraol, etc. was produced. The results relating to the yield of the product, etc. are presented in Table 21.

Example 62

A total of 149.0 mg of ASCA-2 (Pd 4.5 mass %, Pt 0.5 mass %) produced by N.E. Chemcat Corporation (3.5 mol % when calculated based on benzyloxy groups) and tetrabenzyloxysilane (205.5 mg, 0.450 mmol) obtained in Synthesis Example 8 were placed into a two-neck flask equipped with a magnetic stirrer, and 1.6 ml of tetramethylurea ($Me_4Urea$) and aniline ($NH_2Ph$, 7.4 mg) in a 0.044-fold substance amount, when calculated based on benzyloxy groups, were added thereto. After replacing with hydrogen gas, a reaction was conducted for 2.0 h at room temperature. The catalyst was then filtered out with a filter.

The $^1H$, $^{13}C$, and $^{29}Si$-NMR ($Me_4Urea$/THF-$d_8$: −71.7 ppm) analysis confirmed that silanetetraol was produced. The results relating to the yield of the product, etc. are presented in Table 21.

Example 63

The reaction was conducted by the same method as in Example 62, except that the reaction time was changed to 4.0 h. The results relating to the yield of the product, etc. are presented in Table 21.

[C36]

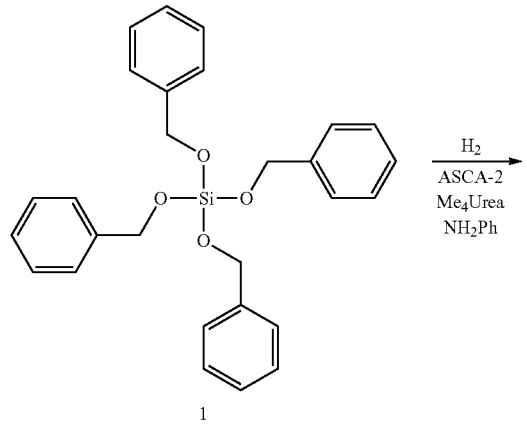

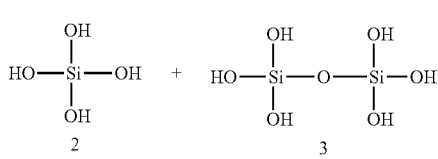

TABLE 21

| | Amount used [mmol] | Amount of ASCA-2 used [mol %] | Reaction time [h] | Conversion ratio [%] | 2 Yield [%] | 3 Yield [%] |
|---|---|---|---|---|---|---|
| Example 61 | 0.300 | 3.5 | 2.0 | 100 | 81 | 12 |
| Example 62 | 0.450 | 3.5 | 2.0 | 100 | 51 | 5 |
| Example 63 | 0.450 | 3.5 | 4.0 | 100 | 60 | 30 |

Example 64

A total of 99.2 mg of ASCA-2 (Pd 4.5 mass %, Pt 0.5 mass %) produced by N.E. Chemcat Corporation (3.5 mol % when calculated based on benzyloxy groups) and tetrabenzyloxysilane (137.0 mg, 0.300 mmol) obtained in Synthesis Example 8 were placed into a two-neck flask equipped with a magnetic stirrer, and 1.6 ml of tetramethylurea ($Me_4Urea$) and aniline ($NH_2Ph$, 4.9 mg) in a 0.044-fold substance amount, when calculated based on benzyloxy groups, were added thereto. After replacing with hydrogen gas, a reaction was conducted for 2.0 h at room temperature. The catalyst was then filtered out with a filter. Concentration was then performed by distilling off the reaction solvent to 357.4 mg under a reduced pressure.

The $^1H$, $^{13}C$, and $^{29}Si$-NMR ($Me_4Urea$/THF-$d_8$: −71.7 ppm) analysis confirmed that silanetetraol, etc. was produced. The results relating to the yield of the product, etc. and the composition are presented in Table 22 and Table 23.

TABLE 22

| | Amount of ASCA-2 used [mol %] | Amount of $NH_2Ph$ used [amine/benzyloxy groups] | Conversion ratio [%] | 2 Yield [%] | 3 Yield [%] |
|---|---|---|---|---|---|
| Example 64 | 3.5 | 0.044 | 100 | 67 | 20 |

TABLE 23

| | | Amount of silanol compound represented by Formula (A) [mass %] | Amount of water [mass %] | Total amount of amine compound and amide compound [mass %] | Other components [mass %] |
|---|---|---|---|---|---|
| Example 64 | After concentration | 5.4 | 0 | 93.1 | 1.5 |

Example 65

A total of 27.2 mg of ASCA-2 (Pd 4.5 mass %, Pt 0.5 mass %) produced by N.E. Chemcat Corporation (2.5 mol % when calculated based on benzyloxy groups) and methyltribenzyloxysilane (54.7 mg, 0.150 mmol) obtained in Synthesis Example 1 were placed into a two-neck flask equipped with a magnetic stirrer, and 1.6 ml of tetramethylurea ($Me_4Urea$) and aniline ($NH_2Ph$, 1.6 mg) in a 0.039-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C-NMR (Me$_4$Urea/THF-d$_8$: −2.4 ppm), and $^{29}$Si-NMR (Me$_4$Urea/THF-d$_8$: −41.1 ppm) analysis confirmed that methylsilanetriol, etc. was produced. The results relating to the yield of the product, etc. and the composition are presented in Table 24.

[C37]

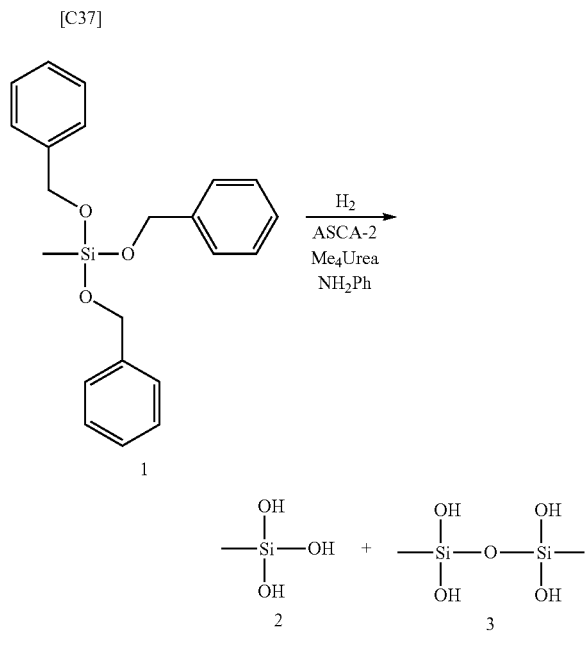

[C38]

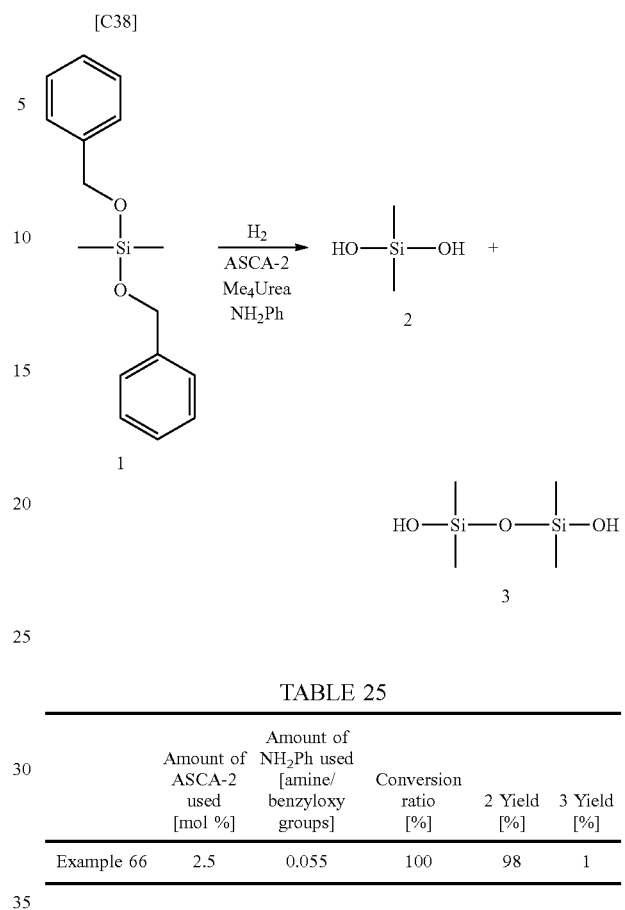

TABLE 24

| Amount of ASCA-2 used [mol %] | Amount of NH$_2$Ph used [amine/ benzyloxy groups] | Conversion ratio [%] | 2 Yield [%] | 3 Yield [%] |
|---|---|---|---|---|
| Example 65 | 2.5 | 0.039 | 100 | 93 | 4 |

Example 66

A total of 17.9 mg of ASCA-2 (Pd 4.5 mass %, Pt 0.5 mass %) produced by N.E. Chemcat Corporation (2.5 mol % when calculated based on benzyloxy groups) and dimethyldibenzyloxysilane (40.8 mg, 0.150 mmol) obtained in Synthesis Example 3 were placed into a two-neck flask equipped with a magnetic stirrer, and 1.6 ml of tetramethylurea (Me$_4$Urea) and aniline (NH$_2$Ph, 1.5 mg) in a 0.055-fold substance amount, when calculated based on benzyloxy groups, were added thereto. After replacing with hydrogen gas, a reaction was conducted for 2.0 h at room temperature. The catalyst was then filtered out with a filter.

The $^1$H, $^{13}$C-NMR (Me$_4$Urea/THF-d$_8$: −2.5 ppm), and $^{29}$Si-NMR (Me$_4$Urea/THF-d$_8$: −9.5 ppm) analysis confirmed that dimethylsilanediol, etc. was produced. The results relating to the yield of the product, etc. and the composition are presented in Table 25.

TABLE 25

| Amount of ASCA-2 used [mol %] | Amount of NH$_2$Ph used [amine/ benzyloxy groups] | Conversion ratio [%] | 2 Yield [%] | 3 Yield [%] |
|---|---|---|---|---|
| Example 66 | 2.5 | 0.055 | 100 | 98 | 1 |

Example 67

A total of 50.2 mg of ASCA-2 (Pd 4.5 mass %, Pt 0.5 mass %) produced by N.E. Chemcat Corporation (3.5 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of tetramethylurea (Me$_4$Urea) and aniline (NH$_2$Ph, 2.4 mg) in a 0.044-fold substance amount, when calculated based on benzyloxy groups, were added thereto. After replacing with hydrogen gas, a reaction was conducted for 2.0 h at room temperature. The catalyst was then filtered out with a filter. Then, tetrabutylammonium chloride (Bu$_4$NCl, 83.4 mg) in a 2.0-fold substance amount, when calculated based on tetrabenzyloxysilane, and 14.4 ml of tetramethylurea (Me$_4$Urea) were added to obtain a composition (solution) including silanetetraol.

The composition was subjected to vacuum freeze drying by freezing using liquid nitrogen (−196° C.) and sublimating tetramethylurea, etc., under reduced pressure (freeze drying step (1) degree of pressure reduction 1 Pa to 3 Pa, shelf temperature −40° C., holding time 12 h; freeze drying step (2) degree of pressure reduction 1 Pa to 3 Pa, temperature increase from a shelf temperature of −40° C. to −15° C. over 12 h; freeze drying step (3) degree of pressure reduction 1 Pa to 3 Pa, −15° C., holding time 18 h). After the drying, the atmosphere inside a glass vial was replaced with an inactive gas and sealed with a rubber stopper, thereby yielding 104 mg of a powdery composition including silanetetraol.

The $^1$H-NMR (DMF-d$_7$/THF-d$_8$: 5.8 ppm), $^{13}$C, $^{29}$Si-NMR (DMF-d$_7$/THF-d$_8$: −69.8 ppm) and IR analysis of the composition confirmed that silanetetraol was included. The composition is described in Table 26, and the IR analysis results relating to the composition are shown in FIG. 1.

[C39]

(A)

Example 8 were placed into a two-neck flask equipped with a magnetic stirrer, and 1.6 ml of tetramethylurea (Me$_4$Urea) and aniline (NH$_2$Ph, 2.4 mg) in a 0.044-fold substance amount, when calculated based on benzyloxy groups, were added thereto. After replacing with hydrogen gas, a reaction was conducted for 2.0 h at room temperature. The catalyst was then filtered out with a filter. Then, tetrabutylammonium chloride (Bu$_4$NCl, 83.4 mg) in a 2.0-fold substance amount, when calculated based on tetrabenzyloxysilane, and 1.6 ml of tetramethylurea (Me$_4$Urea) were added as structure stabilizers to obtain a composition (solution) including silanetetraol.

TABLE 26

|  |  | Amount of silanol compound represented by Formula (A) [mass %] | Amount of water [mass %] | Amount of ammonium salt [mass %] | Total amount of amine compound and amide compound [mass %] | Other components [mass %] |
|---|---|---|---|---|---|---|
| Example 67 | Before freeze drying step | 0.8 | 0 | 0 | 95.8 | 3.4 |
|  | After freeze drying step | 12.9 | 0 | 81.2 | 4.7 | 1.2 |

Example 68

A total of 118 mg of a powdery composition including silanetetraol was obtained by the same method as in Example 67, except that tetrabutylammonium chloride (Bu$_4$NCl) was changed to tetrabutylammonium bromide (Bu$_4$NBr, 96.7 mg).

Figure 2:
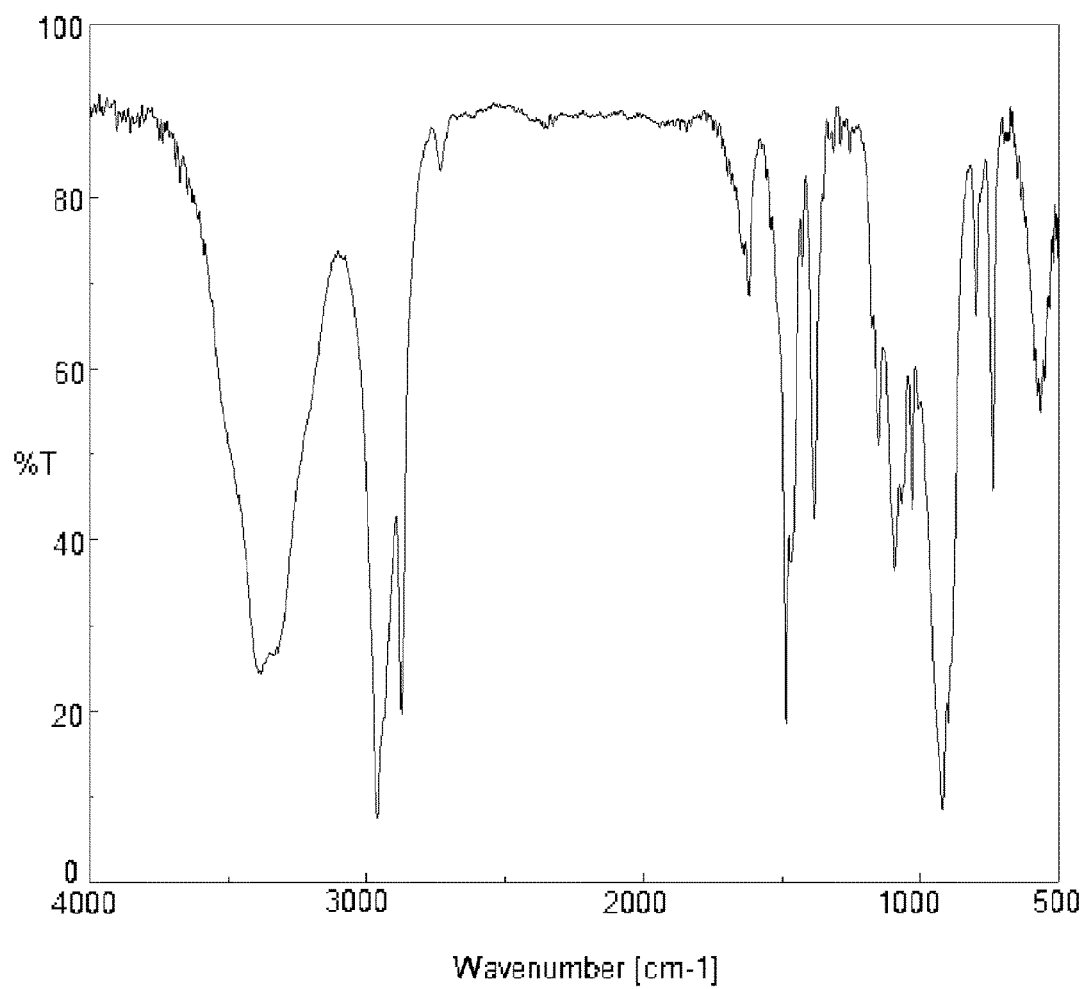
FIG. 2 is a measurement result of IR of the composition obtained in Example 68.

The $^1$H-NMR (DMF-d$_7$/THF-d$_8$: 5.9 ppm), $^{13}$C, $^{29}$Si-NMR (DMF-d$_7$/THF-d$_8$: −70.8 ppm) and IR analysis of the composition confirmed that silanetetraol was included. The composition is described in Table 27, and the IR analysis results relating to the composition are shown in FIG. 2.

TABLE 27

|  |  | Amount of silanol compound represented by Formula (A) [mass %] | Amount of water [mass %] | Amount of ammonium salt [mass %] | Total amount of amine compound and amide compound [mass %] | Other components [mass %] |
|---|---|---|---|---|---|---|
| Example 63 | After freeze drying step | 10.6 | 0.2 | 84.9 | 2.1 | 2.2 |

Example 69

A total of 50.1 mg of ASCA-2 (Pd 4.5 mass %, Pt 0.5 mass %) produced by N.E. Chemcat Corporation (3.5 mol % when calculated based on benzyloxy groups) and tetrabenzyloxysilane (68.4 mg, 0.150 mmol) obtained in Synthesis A total of 2.0 g of diethyl ether (Et$_2$O) was then added to and mixed with the composition, and the solution was placed under a diethyl ether vapor atmosphere and allowed to stay for 24 h, thereby precipitating crystals. The crystals were washed with diethyl ether, and 76.1 mg of a composition (crystals) including silanetetraol was obtained.

Figure 3:
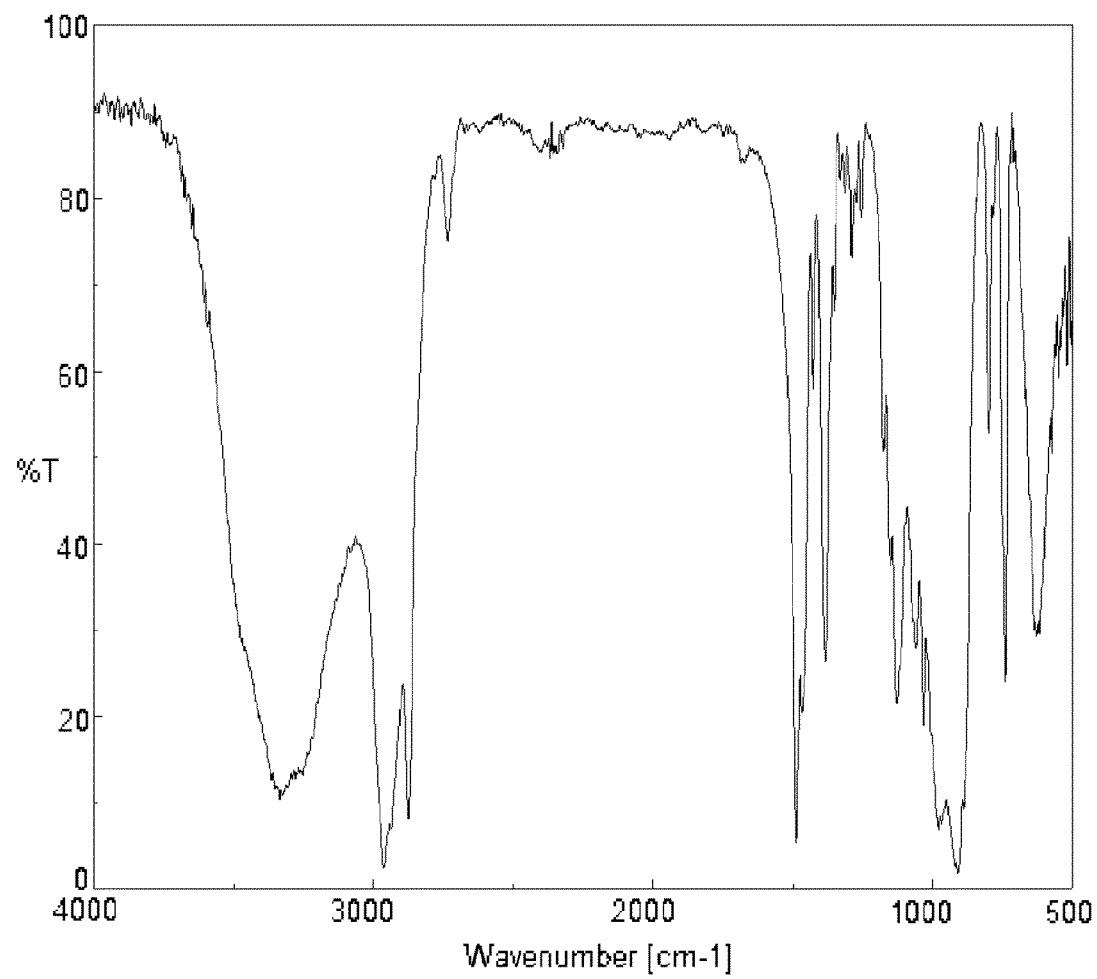
FIG. 3 is a measurement result of IR of the composition obtained in Example 69.

The $^1$H-NMR (DMF-d$_7$/THF-d$_8$: 5.8 ppm), $^{13}$C, $^{29}$Si-NMR (DMF-d$_7$/THF-d$_8$: −69.8 ppm), IR, and X-ray crystal structure analysis of the composition confirmed that silanetetraol was included. The composition is described in Table 28, and the IR analysis results relating to the composition are shown in FIG. 3.

TABLE 28

|  |  | Amount of silanol compound represented by Formula (A) [mass %] | Amount of water [mass %] | Amount of ammonium salt [mass %] | Total amount of amine compound and amide compound [mass %] | Other components [mass %] |
|---|---|---|---|---|---|---|
| Example 69 | After crystallization step | 14.7 | 0 | 85.3 | 0 | 0 |

Example 70

A total of 70.9 mg of a composition (crystals) including silanetetraol was obtained by the same method as in Example 69, except that tetrabutylammonium chloride ($Bu_4NCl$) was replaced with tetrabutylammonium bromide ($Bu_4NBr$, 96.7 mg).

Figure 4:
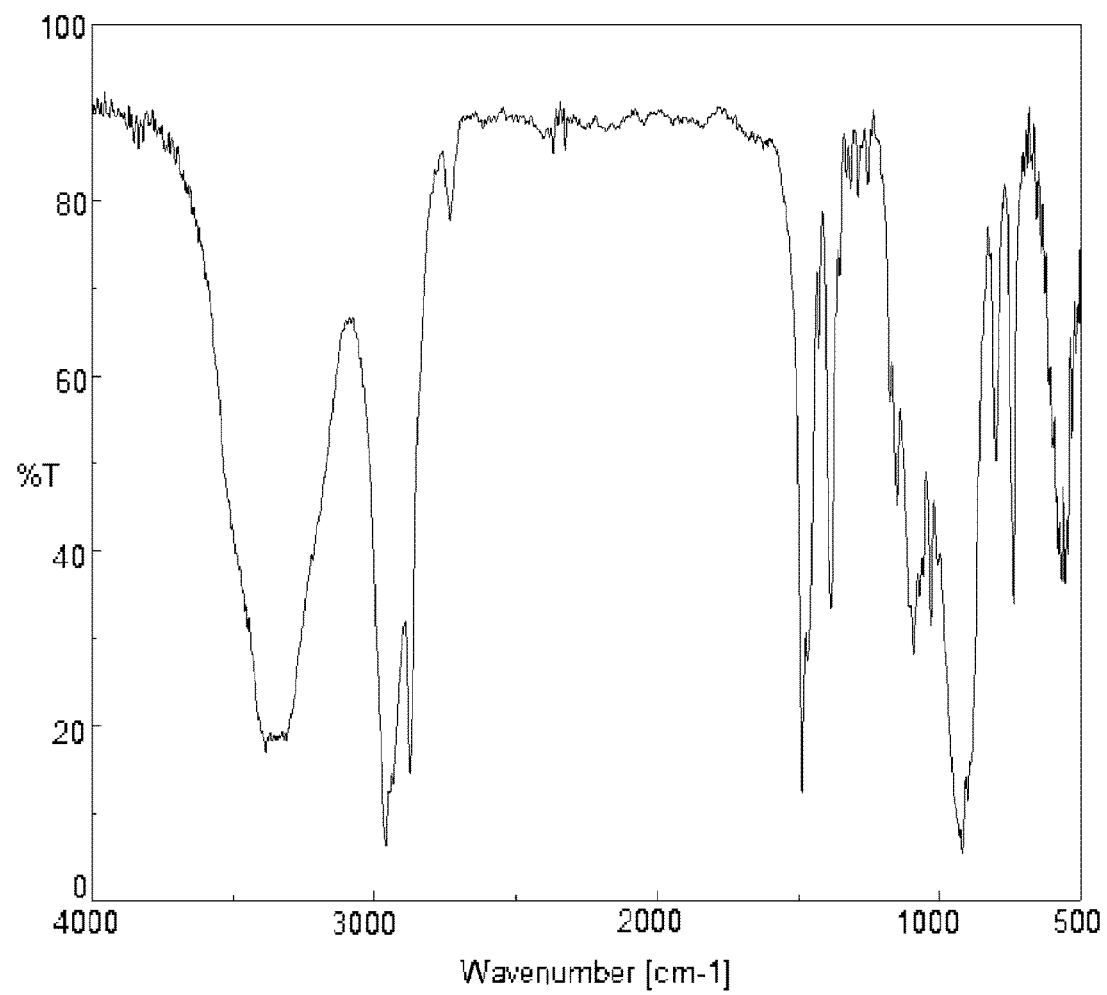
FIG. 4 is a measurement result of IR of the composition obtained in Example 70.

The $^1H$-NMR (DMF-$d_7$/THF-$d_8$: 5.9 ppm), $^{13}C$, $^{29}Si$-NMR (DMF-$d_7$/THF-$d_8$: −70.8 ppm), IR, and X-ray crystal structure analysis of the composition confirmed that silanetetraol was included. The composition is described in Table 29, and the IR analysis results relating to the composition are shown in FIG. 4.

TABLE 29

| | | Amount of silanol compound represented by Formula (A) [mass %] | Amount of water [mass %] | Amount of ammonium salt [mass %] | Total amount of amine compound and amide compound [mass %] | Other components [mass %] |
|---|---|---|---|---|---|---|
| Example 70 | After crystallization step | 13.0 | 0 | 87.0 | 0 | 0 |

Example 71

A total of 50.1 mg of ASCA-2 (Pd 4.5 mass %, Pt 0.5 mass %) produced by N.E. Chemcat Corporation (3.5 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of tetramethylurea ($Me_4Urea$) and aniline ($NH_2Ph$, 2.4 mg) in a 0.044-fold substance amount, when calculated based on benzyloxy groups, were added thereto. After replacing with hydrogen gas, a reaction was conducted for 2.0 h at room temperature.

The catalyst was then filtered out with a filter. Then, an aqueous solution of tetramethylammonium chloride ($Me_4NCl$, 32.9 mg, $H_2O$, 100 μl) in a 2.0-fold substance amount, when calculated based on tetrabenzyloxysilane, was added as structure stabilizer and the system was stirred to obtain a composition (solution) including silanetetraol.

A liquid substance was separated by allowing the composition to stay for 5 min. A tetramethylurea solution of the upper layer and a liquid substance of the lower layer were separated, followed by washing with diethyl ether. The remaining moisture was removed by vacuum drying under reduced pressure, and 36.6 mg of a composition (paste-like) including silanetetraol was obtained.

Figure 5:
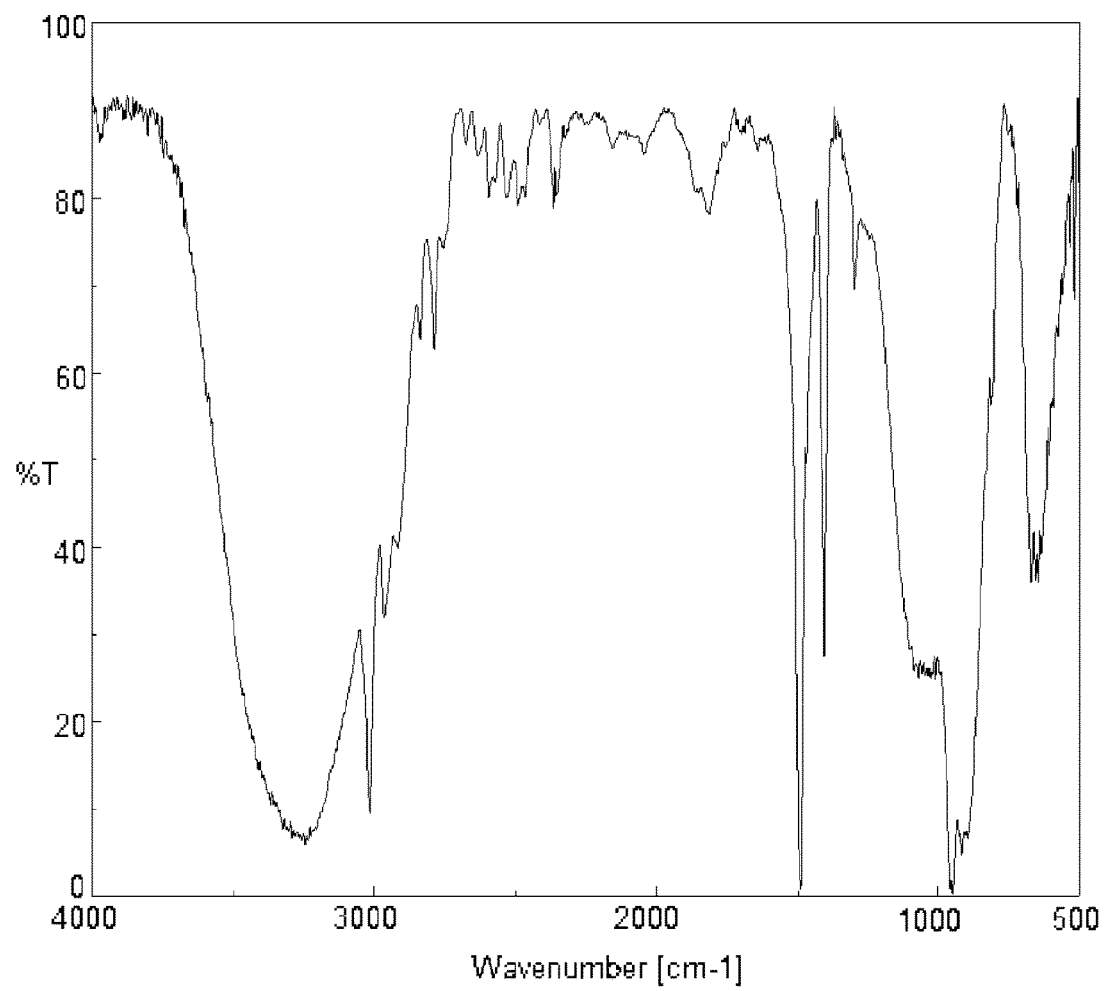
FIG. 5 is a measurement result of IR of the composition obtained in Example 71.

The $^1H$, $^{13}C$, $^{29}Si$-NMR ($D_2O$: −72.3 ppm), and IR analysis of the composition confirmed that silanetetraol was included. The composition is described in Table 30, and the IR analysis results relating to the composition are shown in FIG. 5.

Example 72

A total of 27.2 mg of ASCA-2 (Pd 4.5 mass %, Pt 0.5 mass %) produced by N.E. Chemcat Corporation (2.5 mol % when calculated based on benzyloxy groups) and methyltribenzyloxysilane (54.7 mg, 0.150 mmol) obtained in Synthesis Example 1 were placed into a two-neck flask equipped with a magnetic stirrer, and 1.6 ml of tetramethylurea ($Me_4Urea$) and aniline ($NH_2Ph$, 1.6 mg) in a 0.039-fold substance amount, when calculated based on benzyloxy groups, were added thereto. After replacing with hydrogen gas, a reaction was conducted for 2.0 h at room temperature.

The catalyst was then filtered out with a filter. Then, tetrabutylammonium chloride ($Bu_4NCl$, 83.4 mg) in a 2.0-fold substance amount, when calculated based on methyltribenzyloxysilane, and 14.4 ml of tetramethylurea ($Me_4Urea$) were added to obtain a composition (solution) including methylsilanetriol.

The composition was subjected to vacuum freeze drying by freezing using liquid nitrogen (−196° C.) and sublimating tetramethylurea, etc., under reduced pressure (freeze drying step (1) degree of pressure reduction 1 Pa to 3 Pa, shelf temperature −40° C., holding time 12 h; freeze drying step (2) degree of pressure reduction 1 Pa to 3 Pa, temperature increase from a shelf temperature of −40° C. to −15° C. over 12 h; freeze drying step (3) degree of pressure reduction 1 Pa to 3 Pa, −15° C., holding time 18 h). After the drying, the atmosphere inside a glass vial was replaced with an inactive gas and sealed with a rubber stopper, thereby yielding 93 mg of a powdery composition including methylsilanetriol.

Figure 6:
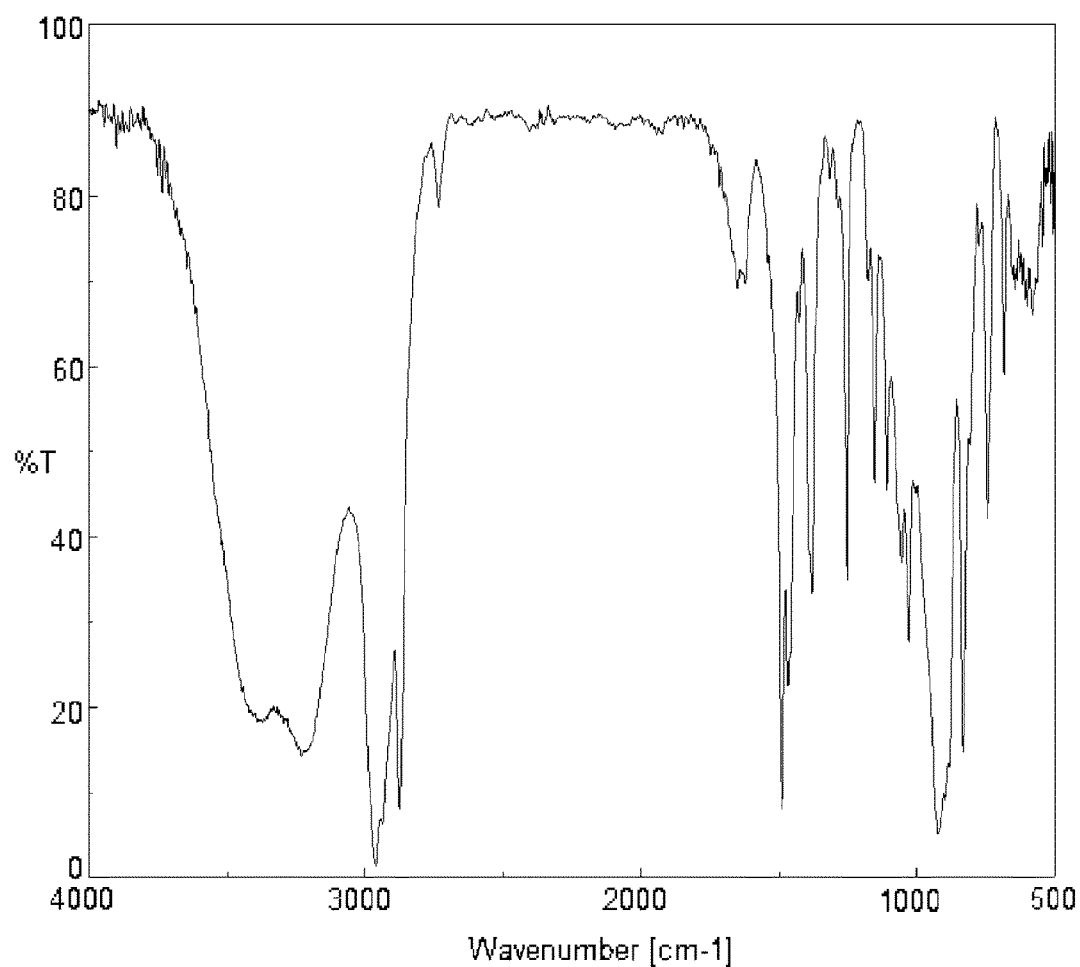
FIG. 6 is a measurement result of IR of the composition obtained in Example 72.

The $^1H$-NMR (DMF-$d_7$/THF-$d_8$: 6.0 ppm), $^{13}C$-NMR (DMF-$d_7$/THF-$d_8$: −2.7 ppm), $^{29}Si$-NMR (DMF-$d_7$/THF-$d_8$: −39.6 ppm) and IR analysis of the composition confirmed that methylsilanetriol was included. The composition is described in Table 31, and the IR analysis results relating to the composition are shown in FIG. 6.

TABLE 30

| | | Amount of silanol compound represented by Formula (A) [mass %] | Amount of water [mass %] | Amount of ammonium salt [mass %] | Total amount of amine compound and amide compound [mass %] | Other components [mass %] |
|---|---|---|---|---|---|---|
| Example 71 | After crystallization step | 27.4 | 0 | 70.2 | 0 | 2.4 |

[C40]

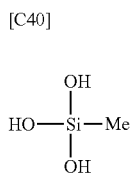

(B-1)

thesis Example 1 were placed into a two-neck flask equipped with a magnetic stirrer, and 1.6 ml of tetramethylurea ($Me_4Urea$) and aniline ($NH_2Ph$, 1.6 mg) in a 0.039-fold substance amount, when calculated based on benzyloxy groups, were added thereto. After replacing with hydrogen gas, a reaction was conducted for 2.0 h at room temperature. The catalyst was then filtered out with a filter. Then, tetrabutylammonium chloride ($Bu_4NCl$, 31.3 mg) in a 0.75-fold

TABLE 31

| | | Amount of silanol compound represented by Formula (B-1) [mass %] | Amount of water [mass %] | Amount of ammonium salt [mass %] | Total amount of amine compound and amide compound [mass %] | Other components [mass %] |
|---|---|---|---|---|---|---|
| Example 72 | Before freeze drying step | 0.7 | 0 | 0 | 96.6 | 1.8 |
| | After freeze drying step | 13.3 | 0 | 85.3 | 0.5 | 0.9 |

Example 73

A total of 117 mg of a powdered composition including methylsilanetriol was obtained by the same method as in Example 72, except that tetrabutylammonium chloride ($Bu_4NCl$) was replaced with tetrabutylammonium bromide ($Bu_4NBr$, 96.7 mg).

Figure 7:
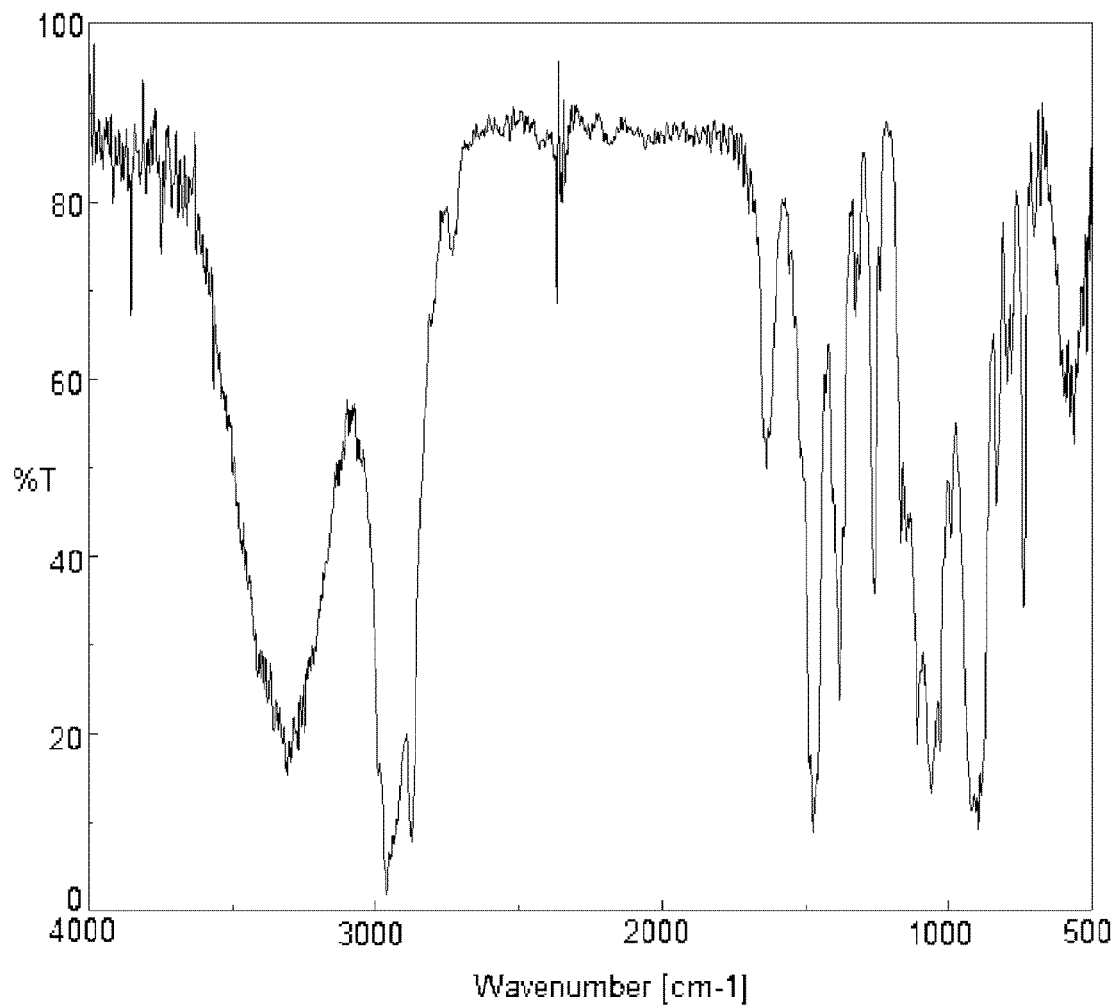
FIG. 7 is a measurement result of IR of the composition obtained in Example 73.

The $^1$H-NMR (DMF-$d_7$/THF-$d_8$: 6.0 ppm), $^{13}$C-NMR (DMF-$d_7$/THF-$d_8$: −2.7 ppm), $^{29}$Si-NMR (DMF-$d_7$/THF-$d_8$: −39.1 ppm) and IR analysis of the composition confirmed that methylsilanetriol was included. The composition is described in Table 32, and the IR analysis results relating to the composition are shown in FIG. 7.

substance amount, when calculated based on methyltribenzyloxysilane was added as a structure stabilizer to obtain a composition (solution) including methylsilanetriol.

A total of 5.0 g of diethyl ether ($Et_2O$) was then added to and mixed with the composition, and the solution was placed under a diethyl ether vapor atmosphere and allowed to stay for 48 h, thereby precipitating crystals. The crystals were washed with diethyl ether, and 18.5 mg of a composition (crystals) including methylsilanetriol was obtained.

The $^1$H-NMR (DMF-$d_7$/THF-$d_8$: 6.0 ppm), $^{13}$C-NMR (DMF-$d_7$/THF-$d_8$: −2.7 ppm), $^{29}$Si-NMR (DMF-$d_7$/THF-$d_8$:

TABLE 32

| | | Amount of silanol compound represented by Formula (B-1) [mass %] | Amount of water [mass %] | Amount of ammonium salt [mass %] | Total amount of amine compound and amide compound [mass %] | Other components [mass %] |
|---|---|---|---|---|---|---|
| Example 73 | After freeze drying step | 7.1 | 0 | 86.7 | 0.7 | 5.5 |

Example 74

Figure 8:
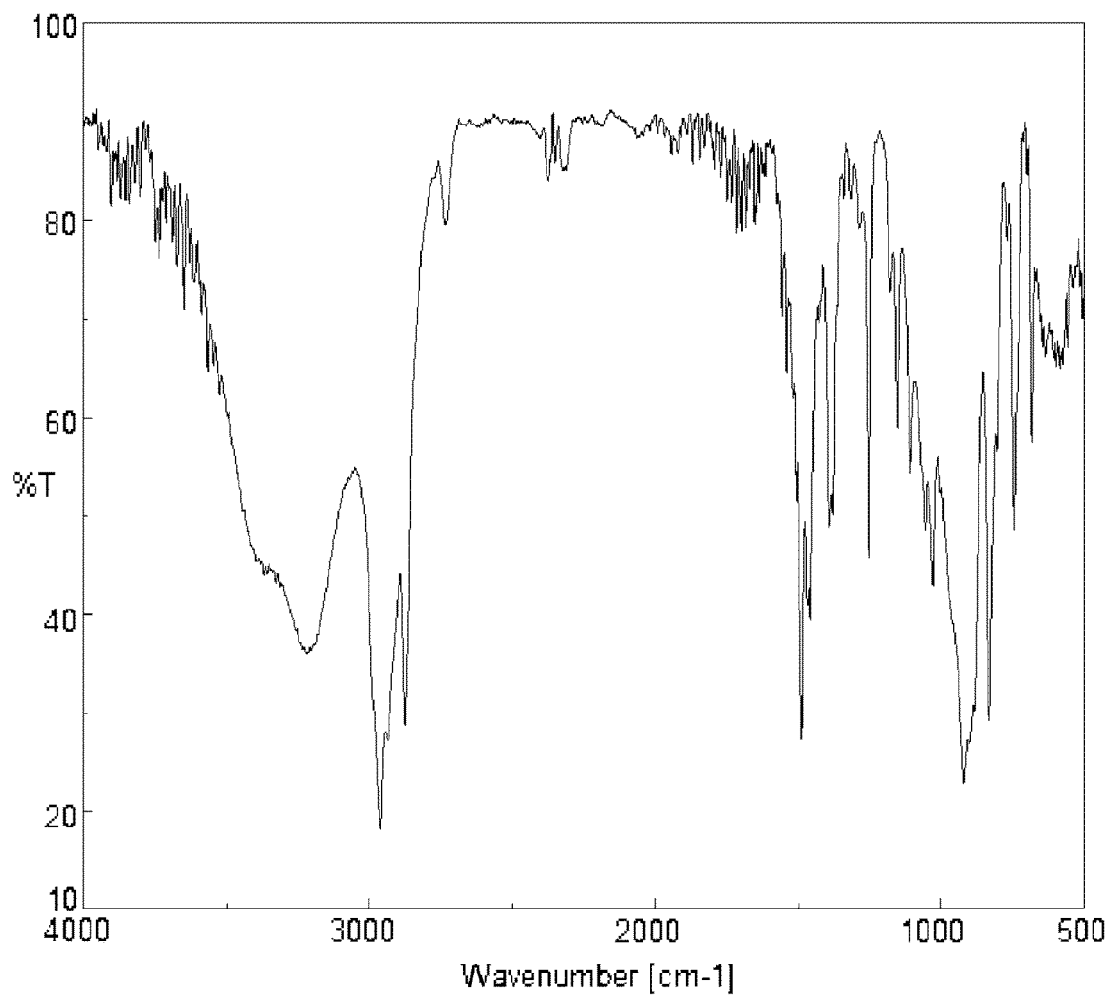
FIG. 8 is a measurement result of IR of the composition obtained in Example 74.

A total of 27.2 mg of ASCA-2 (Pd 4.5 mass %, Pt 0.5 mass %) produced by N.E. Chemcat Corporation (2.5 mol % when calculated based on benzyloxy groups) and methyltribenzyloxysilane (54.7 mg, 0.150 mmol) obtained in Syn- −39.6 ppm), IR, and X-ray crystal structure analysis of the composition confirmed that methylsilanetriol was included. The composition is described in Table 33, and the IR analysis results relating to the composition are shown in FIG. 8.

TABLE 33

| | | Amount of silanol compound represented by Formula (B-1) [mass %] | Amount of water [mass %] | Amount of ammonium salt [mass %] | Total amount of amine compound and amide compound [mass %] | Other components [mass %] |
|---|---|---|---|---|---|---|
| Example 74 | After crystallization step | 14.5 | 0 | 85.5 | 0 | 0 |

Example 75

A total of 18.0 mg of ASCA-2 (Pd 4.5 mass %, Pt 0.5 mass %) produced by N.E. Chemcat Corporation (2.5 mol % when calculated based on benzyloxy groups) and dimethyldibenzyloxysilane (40.8 mg, 0.150 mmol) obtained in Synthesis Example 3 were placed into a two-neck flask equipped with a magnetic stirrer, and 1.6 ml of tetramethylurea (Me$_4$Urea) and aniline (NH$_2$Ph, 1.5 mg) in a 0.055-fold substance amount, when calculated based on benzyloxy groups, were added thereto. After replacing with hydrogen gas, a reaction was conducted for 2.0 h at room temperature. The catalyst was then filtered out with a filter. Then, tetrabutylammonium chloride (Bu$_4$NCl, 83.4 mg) in a 2.0-fold substance amount, when calculated based on dimethyldibenzyloxysilane, and 14.4 ml of tetramethylurea (Me$_4$Urea) were added to obtain a composition (solution) including dimethylsilanediol.

The composition was subjected to vacuum freeze drying by freezing using liquid nitrogen (−196° C.) and sublimating tetramethylurea, etc., under reduced pressure (freeze drying step (1) degree of pressure reduction 1 Pa to 3 Pa, shelf temperature −40° C., holding time 12 h; freeze drying step (2) degree of pressure reduction 1 Pa to 3 Pa, temperature increase from a shelf temperature of −40° C. to −15° C. over 12 h; freeze drying step (3) degree of pressure reduction 1 Pa to 3 Pa, −15° C., holding time 18 h). After the freeze drying, the atmosphere inside a glass vial was replaced with an inactive gas and sealed with a rubber stopper, thereby yielding 89.8 mg of a powdery composition including dimethylsilanediol.

Figure 9:
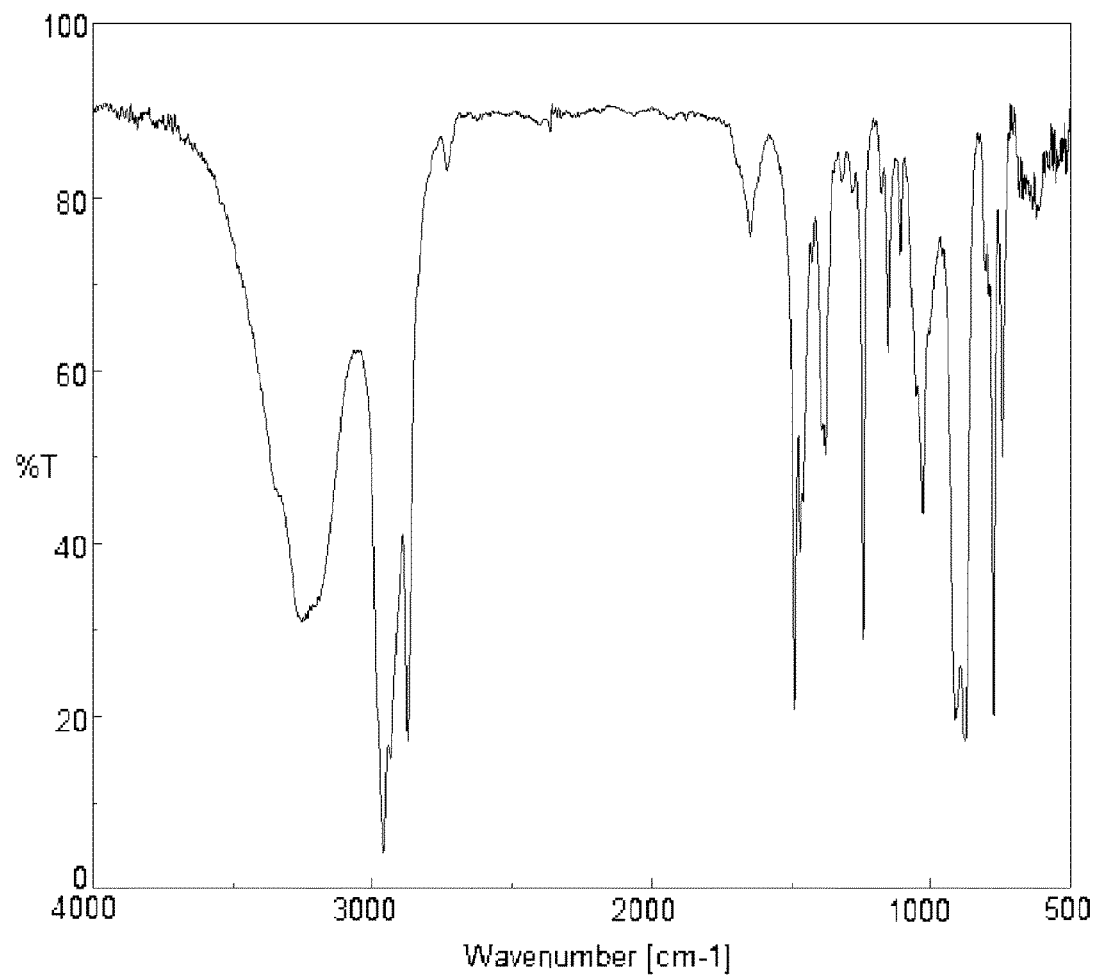
FIG. 9 is a measurement result of IR of the composition obtained in Example 75.

The $^1$H-NMR (DMF-d$_7$/THF-d$_8$: 6.0 ppm), $^{13}$C-NMR (DMF-d$_7$/THF-d$_8$: 0.6 ppm), $^{29}$Si-NMR (DMF-d$_7$/THF-d$_8$: −8.6 ppm) and IR analysis of the composition confirmed that dimethylsilanediol was included. The composition is described in Table 34, and the IR analysis results relating to the composition are shown in FIG. 9.

[C41]

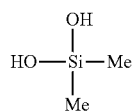

(C-1)

Example 76

A total of 28.8 mg of ASCA-2 (Pd 4.5 mass %, Pt 0.5 mass %) produced by N.E. Chemcat Corporation (2.0 mol % when calculated based on benzyloxy groups) and tetrabenzyloxysilane (68.4 mg, 0.150 mmol) obtained in Synthesis Example 8 were placed into a two-neck flask equipped with a magnetic stirrer, and 1.6 ml of tetramethylurea (Me$_4$Urea) was added thereto. After replacing with hydrogen gas, a reaction was conducted for 2.0 h at room temperature. The catalyst was then filtered out with a filter. Then, tetrabutylammonium chloride (Bu$_4$NCl, 41.7 mg) in a 1.00-fold substance amount, when calculated based on tetrabenzyloxysilane, was added to obtain a composition (solution) including cyclic trisiloxanehexaol.

A total of 2.8 g of diethyl ether (Et$_2$O) was then added to and mixed with the composition, and the solution was placed under a diethyl ether vapor atmosphere and allowed to stay for 48 h at a temperature of −40° C., thereby precipitating crystals. The crystals were washed with diethyl ether, and 3.5 mg of a composition (crystals) including cyclic trisiloxanehexaol was obtained.

Figure 10:
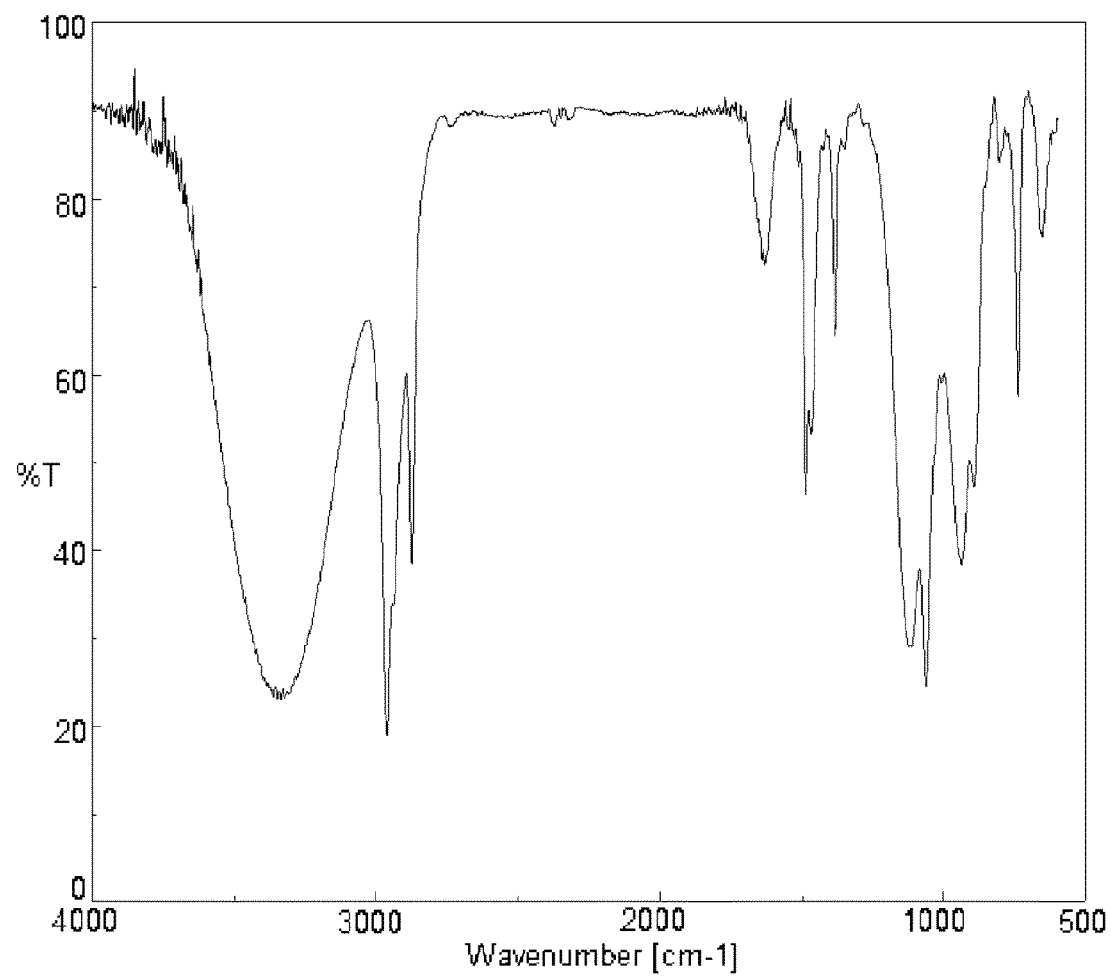
FIG. 10 is a measurement result of IR of the composition obtained in Example 76.

The $^1$H-(DMF-d$_7$/THF-d$_8$: 6.6 ppm), $^{13}$C, $^{29}$Si-NMR (DMF-d$_7$/THF-d$_8$: −81.3 ppm) and IR analysis of the composition confirmed that cyclic trisiloxanehexaol was included. The composition is described in Table 35, and the IR analysis results relating to the composition are shown in FIG. 10.

[C42]

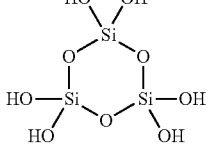

(D)

TABLE 34

| | | Amount of silanol compound represented by Formula (C-1) [mass %] | Amount of water [mass %] | Amount of ammonium salt [mass %] | Total amount of amine compound and amide compound [mass %] | Other components [mass %] |
|---|---|---|---|---|---|---|
| Example 75 | Before freeze drying step | 0.5 | 0 | 0 | 97.4 | 2.1 |
| | After freeze drying step | 13.7 | 0 | 85.4 | 0.6 | 0.3 |

TABLE 35

| | | Amount of silanol compound represented by Formula (D) [mass %] | Amount of water [mass %] | Amount of ammonium salt [mass %] | Total amount of amine compound and amide compound [mass %] | Other components [mass %] |
|---|---|---|---|---|---|---|
| Example 76 | After crystallization step | 27.9 | 0 | 69.6 | 2.5 | 0 |

The composition in accordance with the present invention is useful as, for example, a starting material for siloxane compounds that are used in a variety of fields such as automotive industry, construction industry, electronics, and pharmaceuticals. With the producing method of the present invention, by using corresponding benzyloxy-substituted silanes as starting materials and using heterogeneous catalysts, such as palladium-carbon, which can be easily removed after the reaction, it is possible to produce the respective silanols stably and efficiently. Therefore, with the producing method of the present invention, the structure of the siloxane can be controlled to a high degree, creation of a group of highly functional substances can be expected, and significant industrial effect is obtained. Further, since silanols can be synthesized under anhydrous conditions, compounds which are unstable in water, such as silicon halides, can be allowed to be co-present in the reaction system and to react sequentially with the produced silanol. It is also possible to synthesize alkoxy-substituted silanols which are difficult to synthesize by the conventional hydrolysis method.

The invention claimed is:

1. A composition comprising 5 mass % to less than 100 mass % of a silanol compound represented by the following Formula (D):

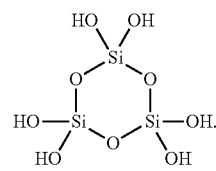

2. The composition according to claim 1, wherein the amount of water is 25 mass % or less.

3. The composition according to claim 1, comprising more than 0 mass % and less than 95 mass % of at least one compound selected from the group consisting of an amine compound and an amide compound.

4. The composition according to claim 3, wherein the amide compound is tetramethylurea.

5. The composition according to claim 1, comprising an ammonium salt, wherein a ratio of the ammonium salt to the silanol compound represented by Formula (D) [(total substance amount of the ammonium salt)/(total substance amount of the silanol compound)] is greater than 0 and equal to or less than 4.

6. The composition according to claim 1, which is a solid body.

* * * * *